(12) United States Patent
Fabijanski et al.

(10) Patent No.: US 7,671,253 B2
(45) Date of Patent: *Mar. 2, 2010

(54) METHODS AND GENETIC COMPOSITIONS TO LIMIT OUTCROSSING AND UNDESIRED GENE FLOW IN CROP PLANTS

(75) Inventors: Steven F. Fabijanski, Orleans (CA); Paul G. Arnison, Orleans (CA); Laurian Robert, Gatineau (CA); Johann Schernthaner, Orleans (CA)

(73) Assignee: Dow AgroSciences LLC, Indianapolis, IN (US)

( * ) Notice: Subject to any disclaimer, the term of this patent is extended or adjusted under 35 U.S.C. 154(b) by 1052 days.

This patent is subject to a terminal disclaimer.

(21) Appl. No.: 10/846,626

(22) Filed: May 17, 2004

(65) Prior Publication Data
US 2005/0283853 A1 Dec. 22, 2005

Related U.S. Application Data

(63) Continuation of application No. 09/886,208, filed on Jun. 22, 2001, now Pat. No. 6,753,460, which is a continuation of application No. PCT/CA99/01208, filed on Dec. 22, 1999.

(60) Provisional application No. 60/113,545, filed on Dec. 22, 1998.

(51) Int. Cl.
  *C12N 15/82* (2006.01)
  *C12N 15/31* (2006.01)
  *A01H 1/02* (2006.01)
  *A01H 5/00* (2006.01)
  *C12N 5/04* (2006.01)
  *C12N 5/10* (2006.01)

(52) U.S. Cl. ................. 800/290; 800/260; 800/271; 800/287; 800/288; 800/306; 435/419; 435/468; 536/24.1

(58) Field of Classification Search ................. None
See application file for complete search history.

(56) References Cited

U.S. PATENT DOCUMENTS 5,689,041 A    11/1997  Mariani et al. ............. 800/205
5,723,763 A    3/1998   Mariani et al. ............. 800/205
5,795,753 A *  8/1998   Cigan et al. ................. 800/274
5,962,769 A *  10/1999  Albertsen et al. ........... 800/303
6,392,119 B1 * 5/2002   Gutterson et al. ........... 800/278

FOREIGN PATENT DOCUMENTS

WO   91/09957   7/1991
WO   96/04393   2/1996
WO   97/40179   10/1997
WO   97/44465   11/1997

OTHER PUBLICATIONS

Ebinuma et al. pp. 25-46 In: Molecular Biology of Woody Plants, vol. 2, Jain et al, eds., Kluwer Academic Publishers: Dordrecht, The Netherlands (2000).*
Ebinuma et al. In Vitro Cellular Development and Biology—Plants 37(2): 103-113 (Mar.-Apr. 2001).*
Sitbon, F. et al Transgenic Tobacco Plants Coexpressing the *Agrobacterium tumefaciens* iaaM and iaaH Genes Display Altered Growth and Indoleacetic Acid Metabolism., Plant Physiol. (1992) 99:1062-1069.
Coliver et al, Plant Md. Biol. 35:509-522, 1997.
Mazzolini et al, Plant Md. Biol. 20:715-731, 1992.
Evans et al, Biochem. Soc. Transactions, 20:344S, 1992.

* cited by examiner

*Primary Examiner*—David T Fox
(74) *Attorney, Agent, or Firm*—Bacon & Thomas, PLLC

(57) ABSTRACT

The present invention relates to methods to control the spread of recombinant DNA molecules between sexually compatible plants of differing genetic composition. The invention describes the production of transgenic plants that comprise recombinant traits of interest or concern linked to repressible lethal genes. The lethal genes are blocked by the action of repressor molecules produced by the expression of repressor genes located at a different genetic locus. The lethal phenotype is only expressed after the segregation of the repressible lethal gene construct and the repressor gene following meiosis. The present invention may be employed for both open-pollinated and hybrid seed production systems and may be used to maintain genetic purity by blocking unintended introgression of genes from plants devoid of the specific repressor gene. The invention includes methods that impart traits that are desirable for environmentally responsible heterologous protein production, to genetic material used to impart said traits and to new plants and products derived by said methods.

36 Claims, 14 Drawing Sheets

METHODS AND GENETIC COMPOSITIONS TO LIMIT OUTCROSSING AND UNDESIRED GENE FLOW IN CROP PLANTS

This is a continuation of U.S. Ser. No. 09/886,208, filed Jun. 22, 2001, now U.S. Pat. No. 6,753,460, which is a continuation of International Application No. PCT/CA99/01208, having an international filing date of Dec. 22, 1999, and which claims priority of U.S. Provisional Application Ser. No. 60/113,549, filed Dec. 22, 1998.

BACKGROUND OF THE INVENTION

The increasing number and diversity of plants containing novel traits derived from recombinant DNA research present both environmental and commercial concerns. The concerns arise from the potential for novel traits to spread by pollen to sexually compatible plants in a natural or cultivated population.

Plants with new and altered traits imparted by genetic technologies and recombinant DNA technology in particular are now viewed as the cornerstone of the crop biotechnology industry. Currently a considerable number of crops plants with novel traits that originated from tissue culture, somatoclonal variation or mutation as well as genetic engineering are undergoing field trials and the first stages of commercial release. These plants not only include conventional crops grown on an annual basis, but other plants such as trees or shrubs which comprise novel traits and are perennial in nature.

Modern crop varieties comprise both individual genes that confer a particular trait and combination of genes assembled through conventional plant breeding. Accordingly, as more novel traits are developed and incorporated into modern crop varieties, it is valuable to have a means to preserve genetic compositions, including those of specific crop varieties, cultivars or breeding lines. Of particular value is the preservation of crops which carry traits not usually found in the crop; for example, plants which produce novel oil, meal or other components or those plants modified to produce speciality chemicals. Additionally, perennial plants such as trees are being produced which carry novel traits such as altered lignin levels, insect and fungal resistance and herbicide tolerance.

Novel traits are introduced into plants by conventional breeding or genetic engineering. However, to date neither route provides features that can be routinely used for maintaining germplasm purity, or controlling persistence or potential spread of the novel trait. Current vectors and genetic compositions typically do not address two important issues: (1) commercial issues such as the prevention of transformed crop plants or elite varieties from contaminating other commercial productions, or the prevention of introgression of alien germplasm from closely related cultivars or plant species, and; (2) environmental issues such as the removal of transformed crop plants or related species that have acquired the genes in question from non-agricultural environments. Additionally current transformation methods do not provide the means for reducing the introduction of genes via pollen mediated out-crossing to other cultivars or related species (either wild or cultivated).

The single largest immediate risk for the use of many crops with novel traits is the risk of contamination among commercial productions of the same crop species. The risk of a crop species such as oilseed rape or canola (*Brassica napus*) to become a weed or to cross with wild weedy relatives is modest compared with the near certainty of crossing with other commercial productions of canola, especially where large production areas exist. In the past this has not been a significant problem for farmers and commercial processors for several reasons. First, breeding objectives have been relatively uniform for canola crop; second, only a small number of cultivars have comprised 90-100% of the total acreage grown by farmers; and third, the only speciality type, traditionally cultivated, high erucic acid industrial oil cultivars have been grown in physical isolation. Accordingly, cross contamination of food quality canola varieties with genes conferring high erucic acid has not been a serious issue.

Recently additional unique varieties have been released. These include varieties that carry recombinant genes which confer tolerance to herbicides and varieties developed by conventional breeding which have variations in fatty acid profile, such as high oleic acid. Purity of seed, both during production and harvesting of canola seed for crushing and processing is now a growing issue. Because of the impending modification of canola with numerous additional recombinant genes that impart different properties to the oil (e.g. high laurate content) or the use of plants as producers of heterologous proteins such as pharmaceuticals, potentially serious industrial cross contamination may be anticipated.

These issues extend to many crops in addition to *Brassica* oilseeds. In maize, increasing emphasis on herbicide tolerance, insect resistance and diversification of modified end products (eg. starch, oil, meal) clearly indicates that many different traits will be incorporated in the corn crop. As some maize varieties are destined for specialized use, such as wet milling or feed, or even production of pharmacologically important proteins, the issue of segregation of these speciality types from the mainstream is relevant. Considering that corn pollen can sometimes travel significant distances, a genetic means to control pollination is be highly advantageous.

Similarly, the proximity of perennial plants to their wild relatives is a problem. For instance, a transgenic tree expressing insect tolerance could cross with a wild species of tree to create a hybrid that expresses insect tolerance. Under managed conditions such as plantations, insect resistance would not have a significant environmental impact. However, should the insect resistance trait become widespread in a natural forest population a serious ecological problem could result. Insect populations are part of the food chain in a forest system and reduced levels of insects could lead to a collapse of the predator population, which is often native bird species. Accordingly, for unmanaged systems control of the spread of genes that may carry environmental consequences is a highly desirable goal.

Currently physical isolation combined with border rows that function as pollen traps have been employed to contain transgenic plants under study and development. This method, however, is impractical for widespread cultivation. Moreover, with increasing production and distribution of an increasing number of different transgenic types, the potential for contamination increases dramatically. This issue has recently become a major concern for the oilseed rape industry and will become a greater issue for other major crops (eg. corn) as the numbers of different recombinant and speciality genotypes reach the market place.

In addition to cross-contamination among commercial crop productions, another concern is the potential spread of crops used as vehicles for producing heterologous proteins of commercial or medicinal value. These novel protein products can potentially contaminate plants destined for food use and export. Although production standards can be implemented that will attempt to preserve the identity of individual transgenic lines and reduce unintended contaminations, the outflow of genes to other cultivars will eventually occur. The potential spread of genes that cannot be easily identified, e.g. by herbicide tolerance, nor impart a distinctive morphology has yet to be addressed by government or industry.

Methods which control the spread of transgenes into the environment or other commercial cultivars are also useful for preventing the introgression of alien germplasm into identity-preserved commercial varieties. In this regard "alien germplasm" is defined as any germplasm which does not comprise the full complement of traits of the identity-preserved cultivar. Accordingly alien germplasm can include both sexually compatible wild relatives and other commercial varieties of the crop. With an increasing number of plants carrying novel traits being contemplated for commercial production, methods that prevent the contamination of both seed production and commodity production will provide a valuable means to maintain germplasm purity and identity preservation.

As an example, many enzymes have been tested that alter plant oil production in oilseed crops such as soybean corn and canola. The same plant species have been used for producing inedible short chain or long chain industrially fatty acids as well as edible oil. Since modified oil seeds must be isolated to ensure pollen carrying the oil modification genes does not contaminate edible oil variety seeds, this poses a growing problem for the seed production industry. The isolation distances routinely practiced in seed production for many crops may not be sufficient to ensure required levels of purity. Where crop plants are used to produce speciality products such as pharmaceutically active compounds, even minor contamination of germplasm is highly undesirable.

Oil seed crops such as canola typically shatter seed before harvest. This results in significant numbers of volunteer plants in subsequent years, potentially contaminating subsequent commercial productions both by crossing and by direct effects of the pollen on developing grain (xenia effects). In addition, seeds retained and distributed by farmers for future planting could contribute to contamination problems.

For perennial plants, the long life of trees and the presence of indigenous wild relatives raise additional concerns. Some trees take many years to flower, producing enormous amounts of pollen that can last for many years and are especially suited for widespread wind pollination. Transgenic trees therefore pose special problems and may require mechanisms to control gene flow to wild relatives.

It has been suggested that some new crop types, through hybridization with wild relatives, may invade natural ecosystems. This and related issues have been extensively debated (eg. University of California, Risk assessment in agricultural biology: proceedings of an international conference, 1990, Casper, R., & Landsman, J., 1992, The bio-safety results of field tests of genetically modified plants and microorganisms. Proceedings of the 2nd International Symposium on The Biosafety Results of Field Tests of Genetically Modified Plants and Microorganisms, 1992 Goslar, Germany, Dale, P. et al., 1992, The field release of transgenic plants. The British Crop Protection Council. Brighton Crop Protection Conference: Pests and Diseases, Vols. I, II and III., Proceedings of the 3rd International Symposium on The BioSafety Results of Field Tests of Genetically Modified Plants and Microorganisms, 1994, Monterey, Calif., D. D. Jones, 1994).

The consensus of these studies and experimental results achieved to date support the view that the degree of potential spread of transgenes to wild relatives is highly dependent upon the species and environmental conditions. Crossing with relatives is not likely with some species and probable for others (Raybould & Grey, J. Applied Ecology 30: 199-219, 1993). Many crops are highly specialized and adapted to non-competitive cultivation practices and thus are not generally considered a serious environmental risk on their own (Dale et al., Plant Breeding 111:1-22, 1993, Fishlock, D., The PROSAMO Report, published by the Laboratory of the Government Chemist, Queens Road, Teddington, Middlesex, UK TW11 0LY) The potential for environmental problems due to, for example, the inclusion of a virus coat protein gene that has potential for viral recombination and the evolution of new viruses with an extended host range, is currently unknown (Gal S., et al., Virology 187:525-533, Grimsley, N., et al., EMBO Journal 5: 641-646, 1986, Lecoq, H., et al., Molec. Plant Microbe Interact. 6:403-406, 1993. Tepfer, M., Biotechnology 11: 1125-1132. 1993). Accordingly there is a need for methods to restrict the potential flow of this type of genes or to selectively eliminate those plants which contain such genes.

Attempts have been made to develop methods to specifically remove or identify plants that contain novel traits introduced by recombinant DNA. For example, the use of a conditionally lethal gene, i.e. one which results in plant cell death under certain conditions, has been suggested as a means to selectively kill plant cells containing a specific recombinant DNA. Recently the development of genes which are conditionally lethal in plants have been described (eg WO 94/03619). However, methods using these genes have been restricted to the application of a substance that triggers the expression of the lethal phenotype. For widespread agricultural practices, these methods have serious limitations.

An example of a conditionally lethal gene is the *Agrobacterium* Ti plasmid-derived oncogene commonly referred to as "gene 2" or "oncogene 2". The gene encodes the enzyme indole acetamide hydrolase (IAMH) that hydrolyzes indole acetamide, a compound that has essentially no phytohormone activity, to form the active auxin phytohormone indole acetic acid. The enzyme IAMH is capable of hydrolyzing a number of indole amide substrates including naphthalene acetamide, resulting in the production of the well known synthetic plant growth regulator naphthalene acetic acid (NAA). Use of the IAMH gene for roguing plants has been described by Jorgenson (U.S. Pat. No. 5,180,873). The method requires application of NAM to discriminate plants which carry the conditionally lethal gene.

Other enzymes may also be used as conditionally lethal genes. These include enzymes which act directly to convert a non-toxic substance to a toxin, such as the enzyme methoxinine dehydrogenase, which converts non-toxic 2-amino-4-methoxy-butanoic acid (methoxinine) to toxic methoxyvinyl glycine (Margraff, R., et al., 1980, Experimentia 36: 846), the enzyme rhizobitoxine synthase, which converts non-toxic 2-amino-4-methoxy-butanoic acid to toxic 2-amino-4-[2-amino-3-hydroxypropyl]-trans-3-butanoic acid (rhizobitoxine) (Owens, L. D, et al., 1973, Weed Science 21: 63-66), the de-acylase enzyme which acts specificlly to convert the inactive herbicide derivative L-N-acetyl-phosphinothricin to the active phytotoxic agent phosphinothricin (Bartsch, K. and Schultz, A., EP 617121), and the enzyme phosphonate monoester hydrolase which can hydrolyze inactive ester derivatives of the herbicide glyphosate to form the active herbicide (Dotson S. B., and Kishore G. M., 1993, U.S. Pat. No. 5,254,801). Other conditionally lethal genes may be engineered from lethal genes. A lethal gene which is expressed only in response to environmental or physiological conditions is lethal under those conditions. For example, a gene that encodes a lethal activity may be placed under the control of a promoter that is induced in response to a specific chemical trigger or an artificial or naturally occurring physiological stress. In this fashion the expression of the lethal gene activity is conditional on the presence of the inducer.

The expression of the conditionally lethal gene that acts on a non-toxic substance to convert said substance to a toxic substance is typically regulated by a promoter that is a constitutive promoter expressed in all or most cell types or a developmentally regulated promoter expressed in certain cell types or at certain stages of development. Any promoter that provides sufficient level of expression can be used. However, in practice promoters that provide high levels of expression for extended periods offer the best opportunities to remove unwanted plants.

The need to apply a chemical to induce the lethal phenotype reduces the utility of a conditionally lethal gene. The widespread application of chemicals may be impractical and raise additional environmental concerns. Accordingly the use of conditionally lethal genes as currently described is not ideally suited for general applications since intervention is required to express the lethal phenotype.

The possibility of using a repressed lethal gene to limit the persistence of hybrid crops has been suggested recently by Oliver et al (patent application WO 96/04393). In this system expression of a lethal gene is blocked by a genetic element that binds a specific repressor protein. The repressor protein is the product of a repressor gene typically of bacterial origin. The genetic element that binds the repressor protein is referred to as a blocking sequence and is constructed such that it further comprises DNA sequences recognized by a DNA recombinase enzyme (e.g. the CRE enzyme). Plants that contain said blocked lethal gene are hybridized with plants comprising the DNA recombinase gene. Either the lethal gene or the recombinase enzyme (or both) is under control of regulatory elements that allow expression only at a specific stage of plant development (e.g. seed embryo). Consequently, the recombinase function in the resulting F1 hybrid plant removes the specific blocking sequence and activates the lethal gene so that no F2 plant is produced. Notably, this scheme cannot control outcrossing of germplasm that carries the novel trait nor introgression of alien germplasm. The method does not apply to self- or open-pollinating varieties. Accordingly, the method is useful only as a means to restrict use (e.g. re-planting) to F1 hybrid seed.

Methods to eliminate recombinant DNA sequences used to obtain transformants such as selectable markers have been developed. Use of a transposase or recombinase to remove selected recombinant sequences from transgenic crop plants has been described in U.S. Pat. No. 5,482,852 (Biologically Safe Transformation System, by Yoder and Lassner). This invention describes a method for removing vector and marker gene sequences by enclosing them within a transposon. The sequences are subsequently removed by crossing the plant to a plant with transposase function.

No published method, however, addresses the problem of contamination of related varieties by cross pollination. The art also does not provide a means to prevent the introgression of alien germplasm by pollination with related pollen, even pollen from the same variety but lacking the genetic trait(s).

Therefore, a method that limits outcrossing and introgression without intervention is needed for management and control of novel traits and crops with novel traits. A mechanism to control cross-contaminations among commercial crops is also needed. Such a mechanism is also needed in the management of perennial crops such as trees, shrubs and grapevines. In particular any mechanism which does not require intervention in order to function is ideally suited for perennial crops. The present invention describes methods and genetic compositions which respond to these needs.

SUMMARY OF THE INVENTION

The present invention comprises methods and recombinant DNA compositions that block the spread and persistence of genes in other cultivars of the same species or related species, resulting from unintended outcrossing by pollen produced by plants containing said recombinant DNA. The invention further ensures that introgression of alien germplasm is eliminated in a selfing population.

The present invention relates to novel recombinant DNA constructs that impart a novel feature to plants containing the recombinant DNA. This feature permits viable seed to be formed only on plants that contain the full complement of the recombinant DNA. The present invention further provides a means to ensure the sexual isolation of germplasm or genetic traits within a defined population through the expression of a trait that is lethal in plants which do not comprise the full complement of the recombinant DNA. The invention ensures that those plants which are fertilized by the transgenic plant but which do not carry the recombinant DNA are unable to form viable seed.

The novel genetic constructs impart no morphologically obvious or easily detectable phenotype to plants. They comprise silent genes that are expressed only when an unintended sexual cross occurs. An unintended cross results in expression of a lethal trait and the undesired plant cells are eliminated. Accordingly the invention restricts the formation of viable seed via outcrossing with sexually compatible species. The novel DNA constructs further provide a means to effectively reduce the introgression of traits from cross-pollination with pollen from sexually compatible species that lack the constructs.

The present invention provides a genetic trait encoded within DNA constructs that ensures that specific cultivars or breeding lines are not contaminated with alien germplasm or contaminate other cultivars and breeding lines. This provides a convenient means to genetically isolate the transgenic plant. The novel DNA constructs may be used as a means to ensure germplasm purity during seed production and the production of the commodity in the field and can be used in both open pollinated and hybrid crop varieties.

Linkage of the novel DNA constructs to DNA molecules that encode novel agronomic or phenotypic traits ensures that the novel agronomic or phenotypic trait does not persist outside of the genotype into which it was introduced. This aspect of the invention is useful in the management of crops with novel agronomic or phenotypic traits or crops with unique combinations of conventional traits developed through plant breeding techniques.

In one embodiment, the invention provides a genetic system comprising two DNA constructs. One DNA construct comprises a dominant repressible lethal gene that, when active, results in cellular death, and whose expression is inhibited in plant cells which contain a second DNA construct comprising a repressor gene, the repressor gene being located at a locus that segregates independently from the repressible dominant lethal gene. The repressor gene encodes a repressor molecule which may be a DNA binding protein, a direct inhibitor of the lethal gene activity, or an RNA, ribozyme or antisense RNA capable of inhibiting the lethal phenotype.

FIG. 1 illustrates the genetic constructs that may be employed in this embodiment of the invention In a preferred embodiment, the dominant repressible lethal gene is under the control of a seed specific promoter and the gene encoding a repressor molecule is located at a locus that segregates independently from the repressible dominant lethal gene. Both the repressible dominant lethal gene and the repressor gene are in the homozygous state. Self pollination maintains this genetic combination.

In another preferred embodiment, the DNA construct further comprises a conditionally lethal gene linked to the repressible lethal gene. The conditionally lethal gene can be activated by the application of a chemical or physiological stress, ensuring a means to completely eliminate the plants or cells containing the recombinant DNA from the environment when required. Accordingly, even self-pollinated cells containing a repressible lethal gene can be selectively removed from a population by virtue of the conditionally lethal gene.

In an additional preferred embodiment, the repressible lethal gene linked to a conditionally lethal gene is linked additionally to a gene encoding a novel trait. A second DNA construct comprises a gene encoding a repressor capable of blocking the activity of the repressible lethal gene. The separate DNA constructs are introduced into the same cells. Linkage of the novel trait to the repressible lethal gene ensures that the novel trait can not persist in related species by transfer through sexual crossing.

In a still further embodiment, the DNA constructs comprising the repressible lethal gene and the repressor gene are within a single recombinant DNA molecule which is introduced into the plant cell. The single recombinant DNA molecule further contains sequences recognized by a site specific recombinase or transposase. Recombinase or transposase activity results in the removal of the repressor gene from the inserted recombinant DNA. As an element of this embodiment, the repressor gene is reintegrated to an independently segregating locus; in particular, to the same locus on the opposite chromosome of a homologous chromosome pair. The DNA constructs that may be employed within the scope of this embodiment are illustrated in FIG. 2.

In another preferred embodiment, DNA constructs are introduced into a plant cell, comprising two repressible lethal genes and two functionally distinct repressors for the repressible lethal genes. The genes are preferably arranged so that the first repressible lethal gene is linked to the repressor capable of repressing the second repressible lethal gene, and the second repressible lethal gene is linked to the repressor capable of repressing the first repressible lethal gene, as illustrated in FIG. 3. Optionally, the constructs comprise a single recombinant DNA molecule which is introduced into the plant cell. The single recombinant DNA molecule contains sequences recognized by a site specific recombinase or transposase, whose activity results in the removal of the first repressible lethal gene and the second repressor from the recombinant DNA. As an element of this optional embodiment, plants are selected wherein the first repressible lethal gene and the linked second repressor gene are reintegrated to an independently segregating locus.

The foregoing embodiments rely on random insertion of the DNA constructs to loci that segregate independently. However, for some applications a means to introduce the recombinant DNA to a specific locus may be desirable. Accordingly, the present invention provides methods to target the recombinant DNA to a specific locus.

The use of a site specific recombinase to introduce recombinant DNA to a locus previously established in the plant genome is contemplated. A recombinase target DNA sequence recognized by a site specific recombinase is inserted into the plant genome by standard transformation procedures. The plant is made homozygous for the target DNA sequence by known methods such as selfing and selection or anther or isolated microspore culture. Alternatively a plant homozygous for said inserted sequence can be made directly by transformation of haploid cells or tissue, followed by chromosome doubling.

The appropriate recombinase expressible in plant is inserted by any of several methods such as transformation, microinjection, electroportation, etc. into plant cells homozygous for the target DNA sequence. The plant cells are then independently re-transformed with DNA constructs comprising either the repressible lethal gene or the repressor gene. These DNA constructs have been modified to include site specific recombinase recognition sequences such that the DNA construct can be inserted into the pre-existing recombinase target DNA sequence. Accordingly, plant lines are recovered that contain either the DNA construct comprising the first repressible lethal gene or the first repressor gene. By crossing said lines, plants may be recovered that contain both introduced DNA constructs (repressible lethal gene and repressor) at the same genetic locus on opposite chromosomes of a homologous chromosome pair.

Accordingly the site-specific insertion method comprises preparation of DNA constructs comprising a repressible lethal gene and in some embodiments a dominant conditionally lethal gene. The method also comprises preparation of a repressor gene which can be inserted concomitantly or independently of the lethal gene. The repressible lethal gene is repressed by the repressor encoded by the repressor gene, conveniently located at a chromosomal site that segregates independently of the inserted repressible lethal gene. It is within the scope of the present method to employ site-specific recombination as a means to target repressor and repressible lethal genes to specific sites within the plant genome, in particular to those sites at which specific recombinase recognition sites have been inserted. An illustration of the DNA constructs and steps that may be employed in this embodiment of the invention are shown in FIG. 4.

The invention provides methods and compositions that allow the genetic purity of transgenic plants to be maintained by simple self pollination in open pollinated crops. No intervention is required. The invention further provides methods for the convenient preparation, propagation and husbandry of plants containing the recombinant DNA. Genetic compositions are provided for use in open pollinated and hybrid plant production systems. Illustration of the utility of the method as employed with open pollinated crops such as *Brassica napus* oilseed is shown in FIG. 5, illustration of the utility of the method as employed with hybrid crops such as maize is shown in FIG. 6.

During the production of pollen, the repressible lethal gene is segregated from the repressor gene, in accordance with the genetic schemes described above. Subsequently any outcrossed plants (i.e. those plants that have inadvertently received pollen that carries the repressible lethal gene) cannot form viable seed because the newly formed seed contains no repressor to repress expression of the lethal gene. The lethal gene is repressed in selfed plants because these plants retain both lethal and repressor genes. For those embodiments which further comprise a conditionally lethal gene linked to the repressible lethal gene, plants containing these genes can be eliminated by application of a chemical or physiological stress to activate the conditionally lethal gene.

The present invention provides methods and compositions for the production of recombinant plants with substantially reduced or zero risk of gene transfer via crossing. In some embodiments, the plants can be safely and specifically removed from the growing site by application of an inexpensive and environmentally benign chemical.

The invention is well suited to the production of crop plants for large scale agricultural and industrial applications where the potential contamination of other commercial productions of the same species, via cross pollination or volunteer seed, is to be avoided. The invention further provides a mechanism of safe use and environmental protection for recombinant plants that may cause environmental damage by invasion of other habitats or that may spread their transgenes by crossing by crossing with wild weedy relatives.

The present invention provides specifically a method for producing crop plants as heterologous protein producers, without risk of contaminating other commercial productions of the same species.

The invention further provides a means to control the introgression of alien germplasm into commercial plant varieties and to maintain genetic purity of lines comprising the introduced genes. It is noted that the DNA constructs comprising these genes can be used with or without being linked to a novel trait gene to provide a means of ensuring genetic purity during seed production or production of the commodity.

For some crops, such as self-incompatible crops, the invention improves hybrid seed production via self-incompatibility. In this particular embodiment of the invention, a self-incompatible female parent is modified to carry the repressible lethal gene but not the repressor gene. The female line is unable to form viable seed. Crossing this self-incompatible female parent with pollen that carries a repressor gene results in the production of viable hybrid seed that carries both the repressible lethal gene and the repressor gene. Linkage of a novel trait such as insect resistance to the repressible lethal gene would further prevent the dissemination and persistence of the trait in related species.

The use of repressible lethal genes in self-incompatible crops eliminates the problems of breakdown of self-incompatibility in the female parent often seen in commercial seed production. This breakdown problem leads to self-seed contamination of the hybrid seed. By using repressible lethal genes, self-seed is not possible on the female parent since it lacks the repressor and is self-incompatible. A convenient means to maintain the female line (such as use of a repressor inducible under certain conditions) can be employed to increase the number of female parents. Alternatively, the line can be clonally propagated. Current mechanisms to overcome self-incompatibility include elevated carbon dioxide and other stress treatments. It is within the scope of the invention to use promoters that are inducible under the same conditions as those used to overcome self-incompatibility, as this provides a particularly convenient means to increase seed production of the female parent. The method is particularly useful for production of *Brassica* vegetable crops where self incompatibility is commonly applied.

The following terms are defined and used within the scope of this invention.

Alien germplasm: a gene or combination of genes or genetic traits which is not part of the specific genetic makeup of an individual crop plant or variety.

Blocking or "blocks": the inhibition of a lethal gene activity by a repressor; blocking can include: the prevention of RNA transcription by binding of a repressor to a specific DNA sequence, binding of an antisense RNA or ribozyme to a primary RNA or mRNA transcript, binding of an inhibiting factor to a lethal gene product such as a RNAse or protease inhibitor binding to a toxic ribonuclease or toxic protease. Any method which prevents the expression of a lethal phenotype can be considered as "blocking" the lethal phenotype.

Conditionally lethal gene: a gene which confers on a plant cell a phenotype which renders the plant cell sensitive to an agent, said agent may be genetic or chemical in nature, said sensitivity ultimately leading the death of the plant cell.

Constitutive promoter: a DNA sequence capable of causing gene expression in substantially all plant cells, tissues and organs.

De-repressed lethal gene: a lethal gene that expresses the lethal phenotype due to the absence of a functional repressor.

Gene: a DNA expression cassette comprising a transcribed region under the control of a promoter further comprising a transcription termination signal.

Inducible promoter: a DNA sequence capable of causing gene expression in response to a chemical, physical or environmental inducer.

Introgression: the undesired movement of a gene or genes through sexual crossing, usually by pollen, from a plant which is not intended to be the pollen donor for the formation of seed.

Lethal gene: a gene, that when expressed in a plant cell ultimately leads to the death of the plant cell.

Lethal gene activity: a genetic activity that leads to plant cell death. A lethal gene activity can be due to a single gene or can also be the result of the combined expression of more than one gene.

Oncogene: a gene encoding an enzyme involved in tumor formation or abnormal plant growth as a result of infection of susceptible plants by *Agrobacterium* sp. Known oncogenes include those comprising the tmr and tms loci of the T-DNA region of the Ti plasmid.

Outcrossing: the movement of pollen from a plant of one genetic type to a sexually compatible plant of a different genetic type. Outcrossing is generally used to describe the unintended movement of pollen; however in some plant species, particularly those which are self-incompatible, outcrossing is also used to represent the normal pollination events within a population of incompatible plants.

Promoter: a DNA sequence capable of causing gene expression in a plant cell.

Repressor: a gene product that can specifically block the activity of a gene product or expression of a gene. A repressor can be a protein, RNA or a specific substance produced by the activity of a repressor gene product.

Repressor binding site: a DNA sequence that is recognized specifically by a repressor, said recognition leading to the inhibition of expression of a gene containing said repressor binding site. In some embodiments a repressor binding site may also represent a RNA sequence which is recognized by a ribozyme or antisense RNA.

Repressor gene: a DNA expression cassette capable of expressing a functional repressor.

Repressed lethal gene: a lethal gene where the lethal phenotype that is a result of the gene activity is blocked by the presence of a repressor.

Repressible lethal gene: a lethal gene, the expression of which can be inhibited by the action of a specific repressor molecule.

Responsive to a repressor: a lethal gene or lethal gene product the lethal activity of which is inhibited in response to the presence of a repressor of lethal gene activity.

Selfing: self-pollination leading to the formation of a seed or reproductive structure.

Tissue specific promoter: a DNA sequence capable of causing substantial gene expression only in a specific plant cell, organ or tissue.

Transcribed region: a DNA sequence that is transcribed under the control of a promoter. Said DNA sequence may encode a RNA capable of being translated into a protein or may encode a RNA that can specifically inhibit or prevent the expression of a gene.

Transcription termination sequence: a DNA sequence that defines the termination of transcription.

According to this scheme, an elite parental line is transformed with a target recombinase sequence. Hemizygous plants are recovered and converted to homozygous state. The plants are re-transformed with a repressible lethal gene or a repressor gene flanked by recombinase target sequence(s). Plants are recovered that comprise randomly integrated SL or R. Recombinase function is then used to specifically excise and insert SL or R into the target recombinase sequence present on the target chromosome pair. Plants are recovered which contain SL and R on opposite sister chromosomes of a chromosome pair.

Figure 1:
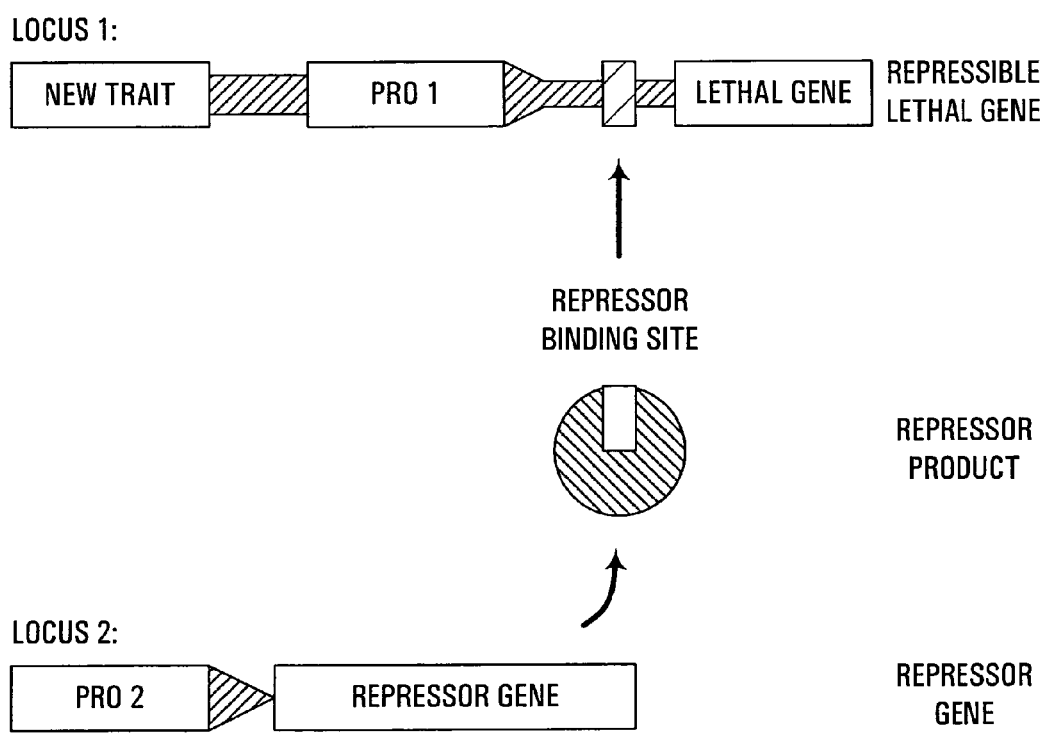
FIG. 1 illustrates a scheme wherein a repressible lethal gene and a repressor gene are located at independently segregating loci. The term "new trait" represents a linked recombinant DNA or a specific genotype which comprises a combination of one or more traits. PRO 1 represents the promoter controlling expression of the repressible lethal gene; a seed specific promoter is preferred. Sufficient expression of the repressor gene prevents expression of the lethal phenotype.
Figure 2:
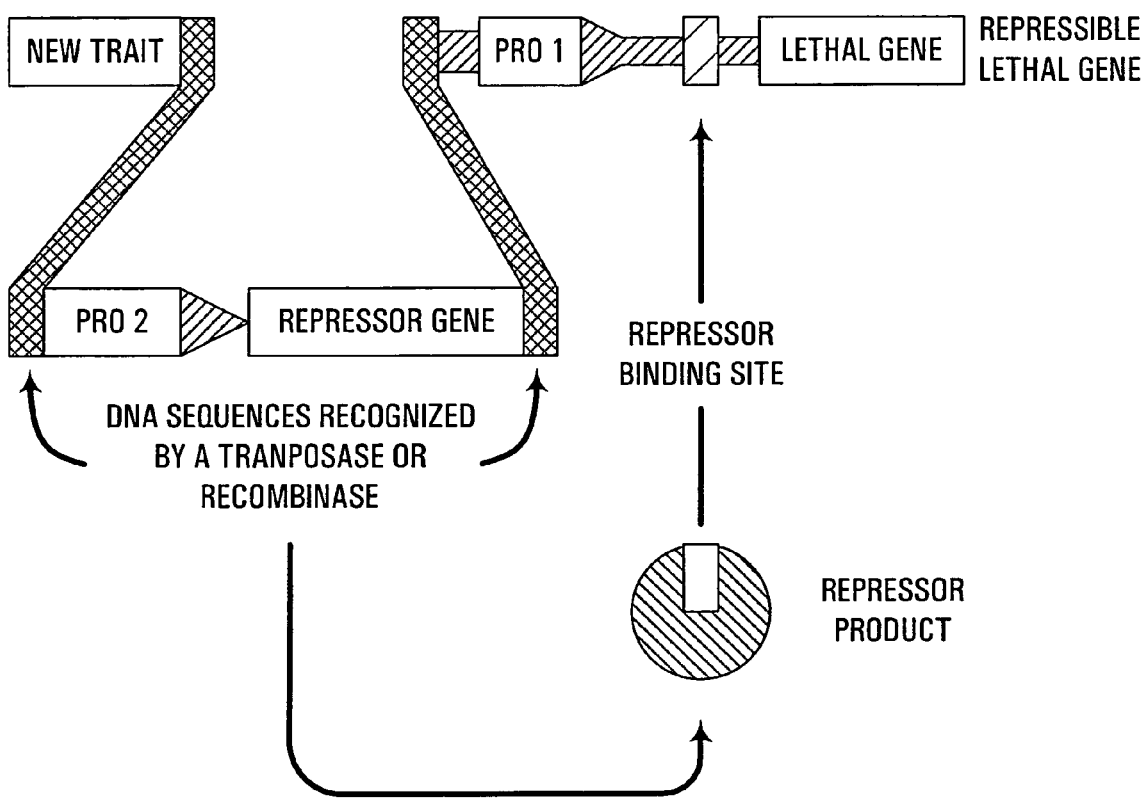
FIG. 2 illustrates a DNA construct comprising both the lethal gene and the repressor gene. The repressor gene can be specifically targeted to a new chromosomal location by the use of a site specific recombinase or transposase. The transposase or recombinase recognition sequences allow the repressor gene to be re-located, in the presence of active recombinase or transposase enzyme, to a locus which segregates independently of the repressible lethal gene.
Figure 3:
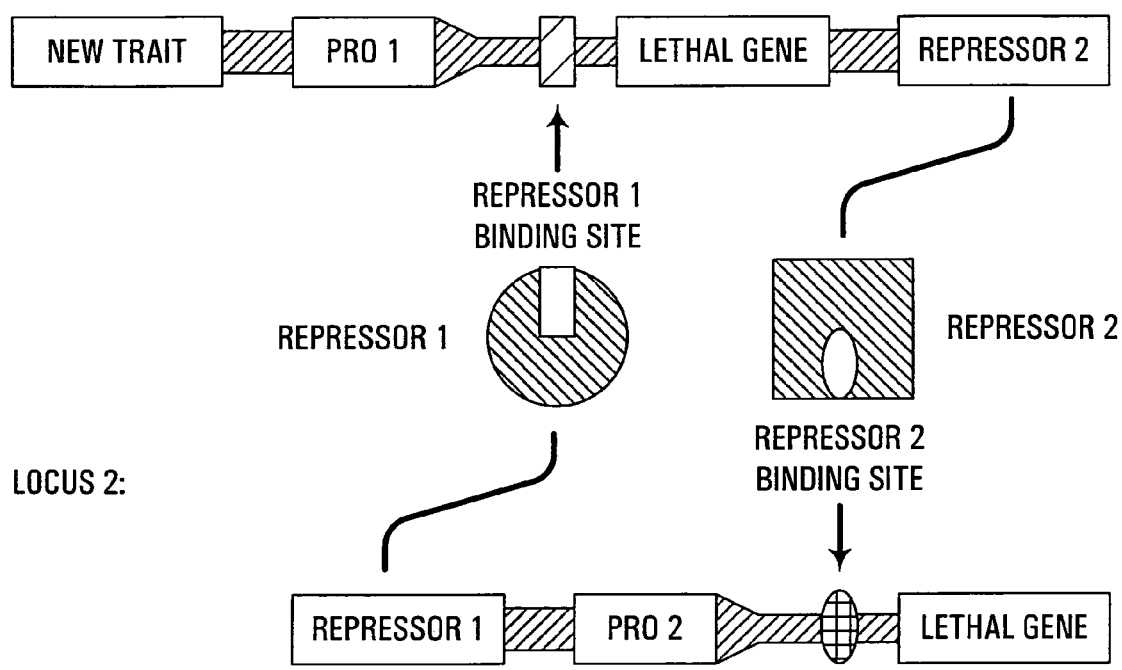
FIG. 3 illustrates DNA constructs comprising two repressible lethal genes and two independent repressor genes. The new trait or traits can be linked to one or both or the repressible lethal genes. The repressor genes are functionally distinct, i.e. they act independently. The repressible lethal genes may encode the same or different repressible lethal gene activity. PRO 1 and PRO 2 may be the same or different promoters; seed specific promoters are preferred.
Figure 4:
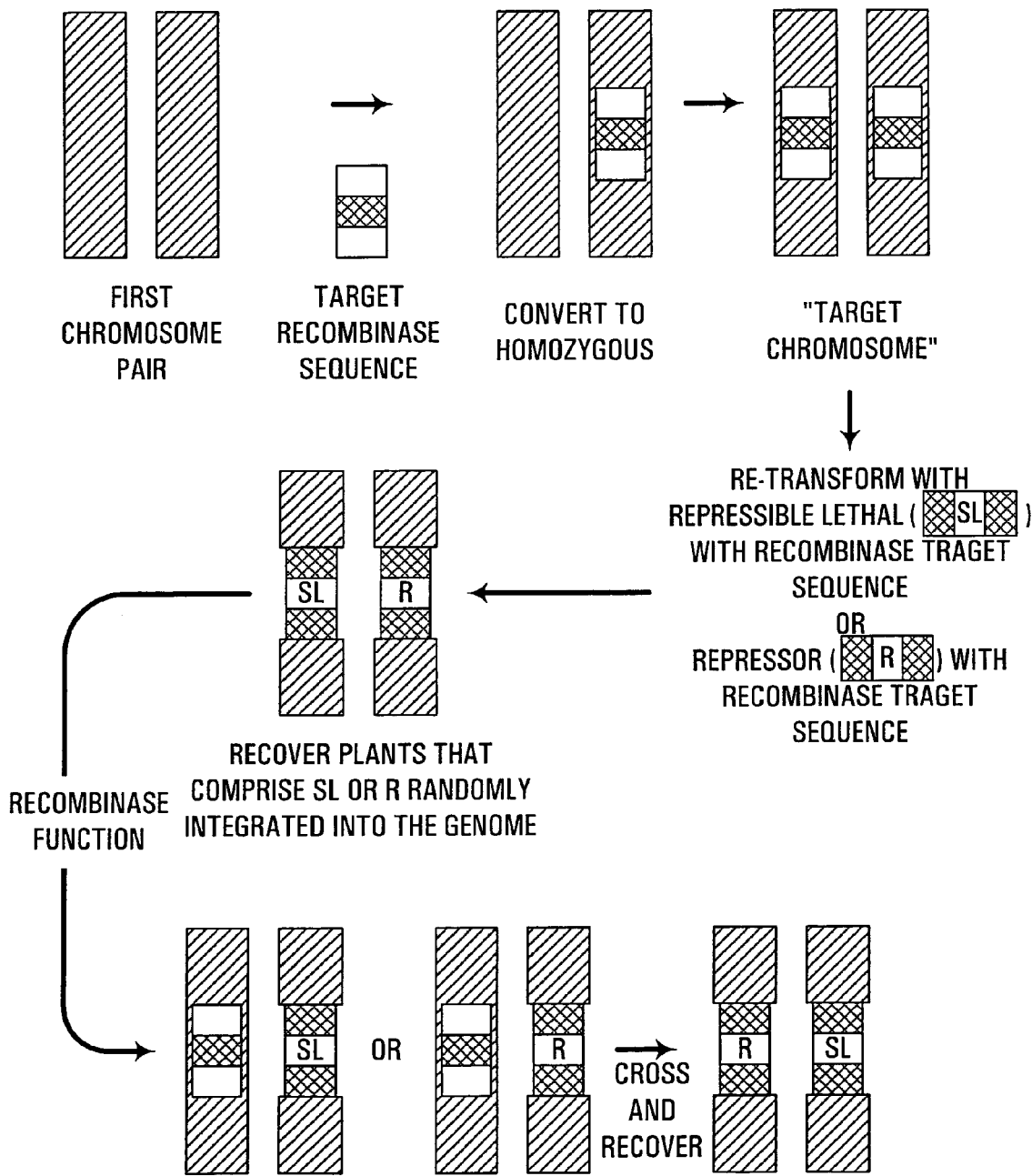
FIG. 4 illustrates the scheme for producing plants containing a repressible lethal gene where the repressor and lethal genes are located on opposite chromosomes of a homologous chromosome pair. A site-specific recombinase targets the repressor and lethal gene constructs to opposite sister chromosomes of a homologous chromosome pair. The "Target Recombinase Sequence" may further comprise an inactive selectable marker which is activated upon insertion of the construct.
Figure 5:
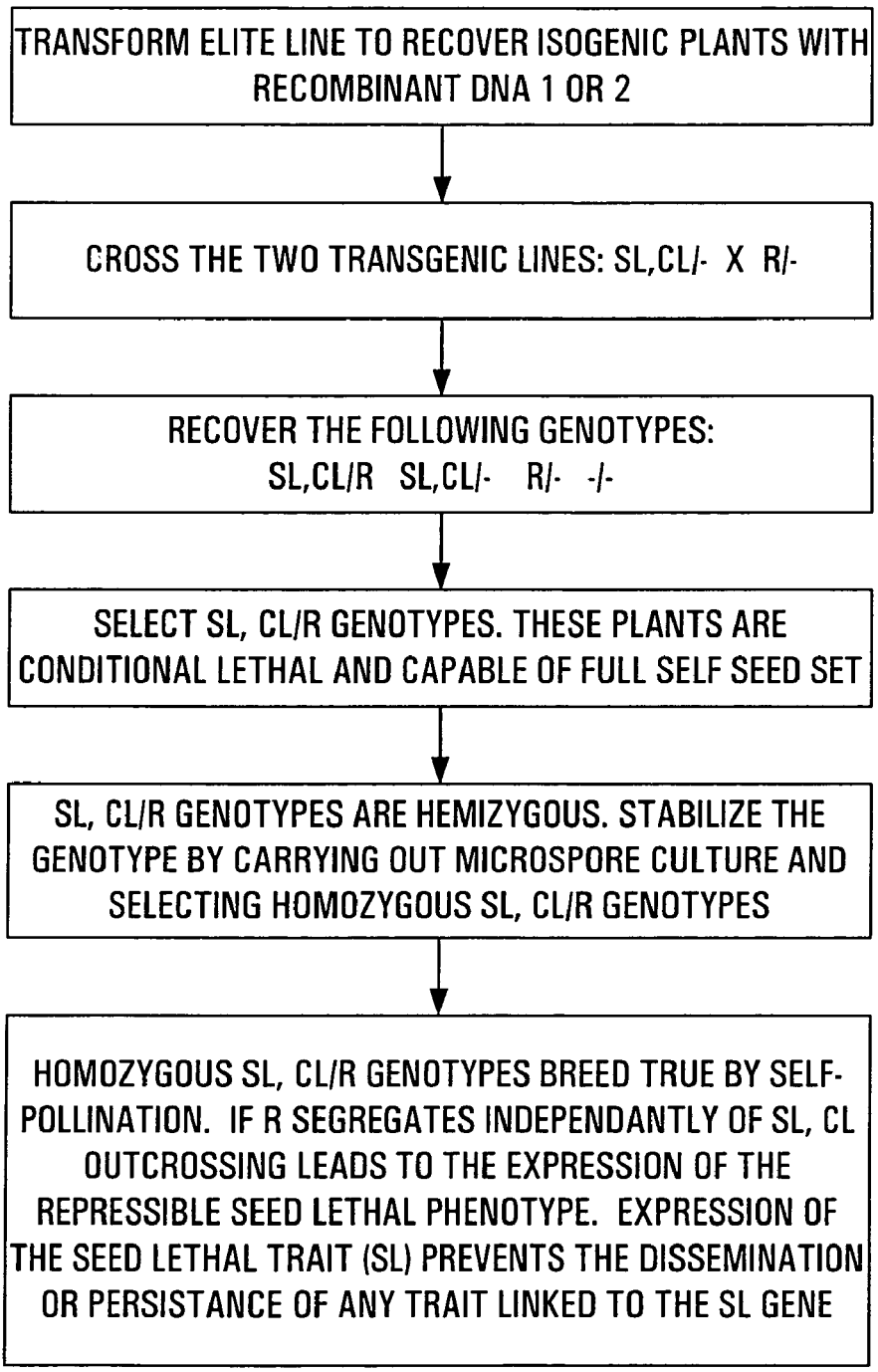

FIG. 5 illustrates the use of a repressible lethal gene in self pollinating crops. Use of a conditionally lethal gene is optional.

In this figure, Recombinant DNA 1 is Repressible Seed Lethal (SL) and Conditional Lethal in Other Tissues (CL). Recombinant DNA 2 is a Repressor.

Figure 6:
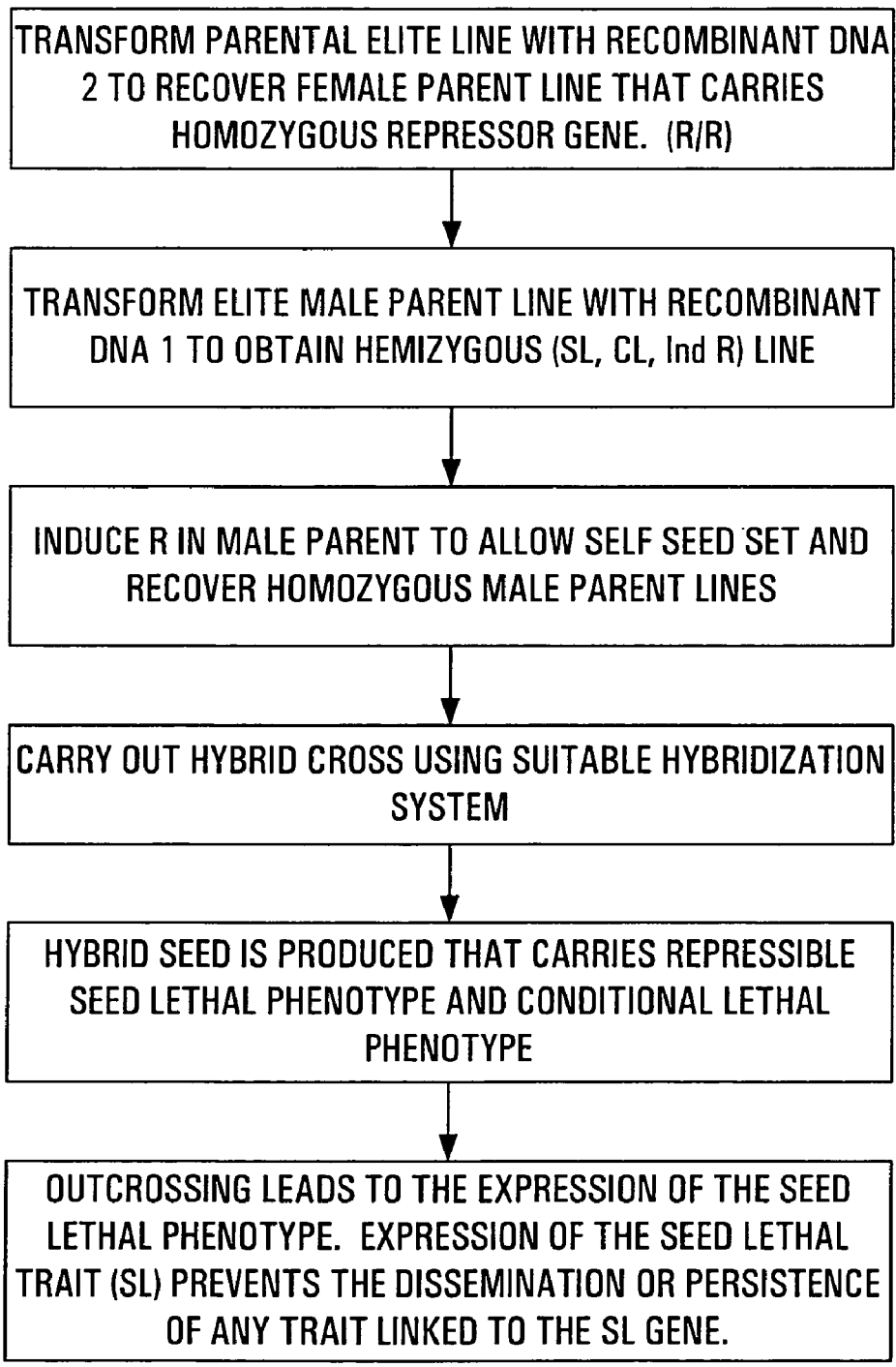

FIG. 6 illustrates the use of a repressible lethal gene method in hybrid crops. Use of a conditionally lethal gene is optional.

In this figure, Recombinant DNA 1 is Repressible Seed Lethal (SL), Conditional Lethal in Other Tissues (CL), also including an Inducible Repressor (IndR). Recombinant DNA 2 is Non-Lethal Repressor (R).

Figure 7A:
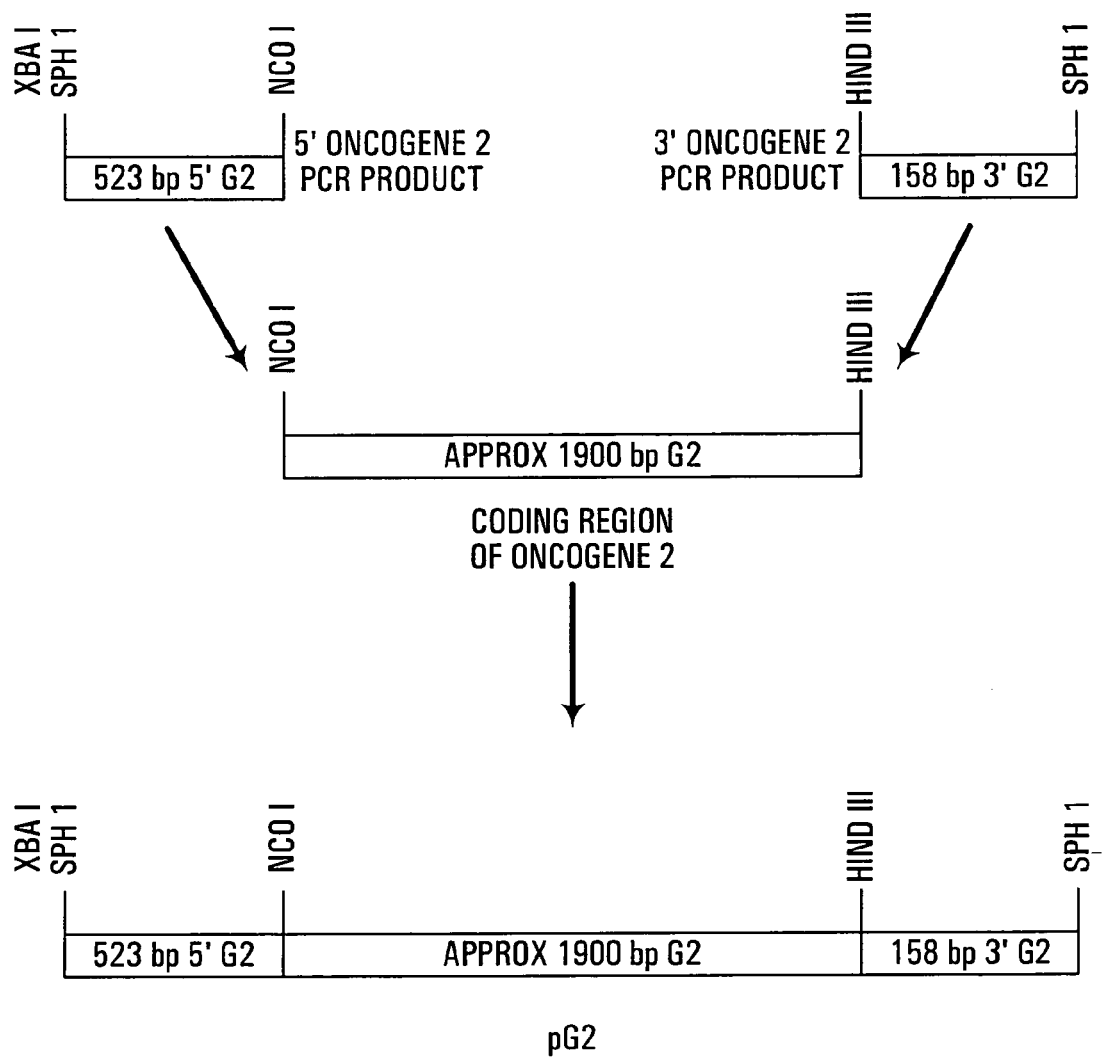
Figure 7B:
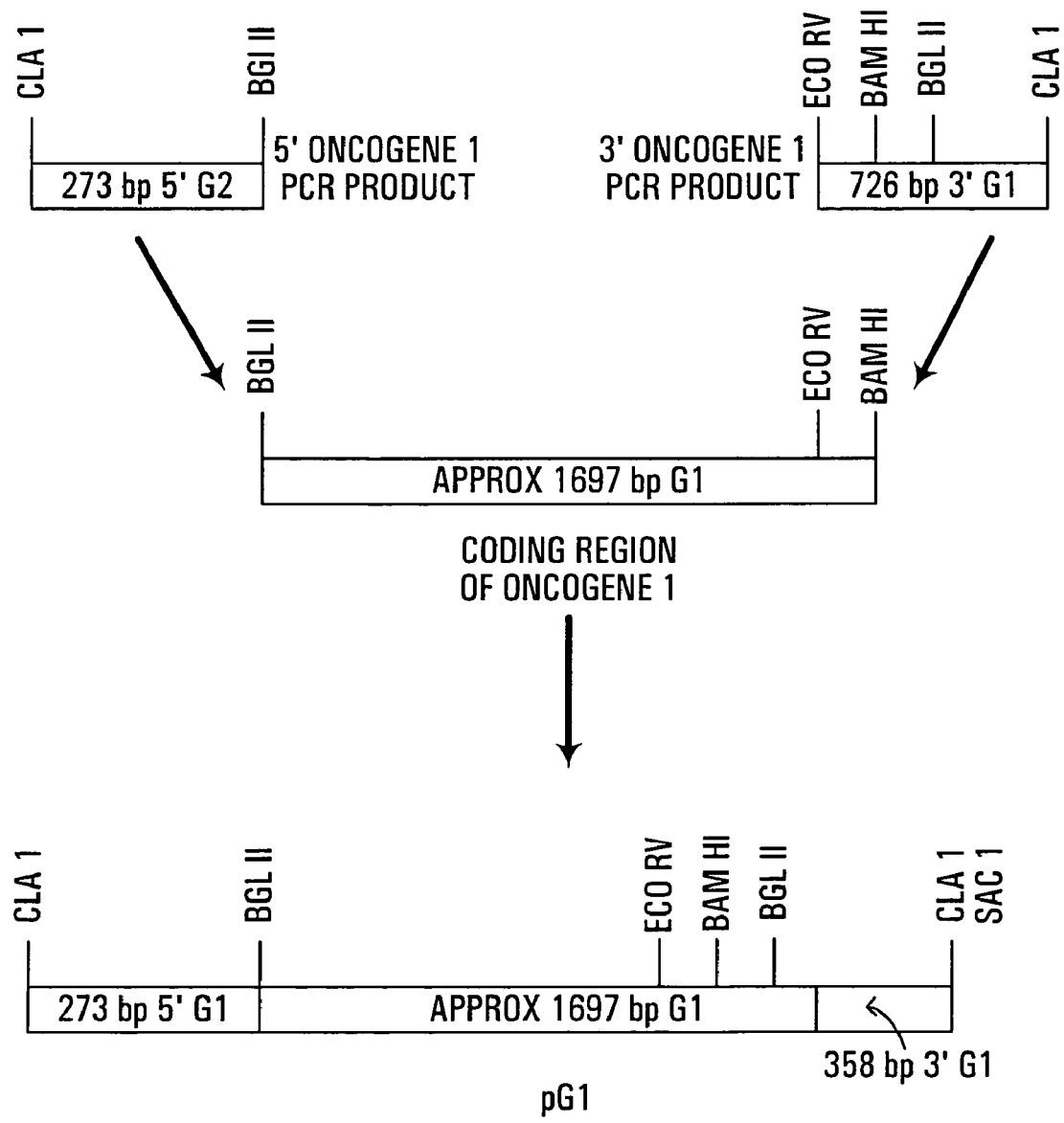

FIGS. 7A and 7B illustrate the isolation of the lethal genes oncogenes 2 (FIG. 7a) and 1 (FIG. 7b) from the Ti plasmid pTi15955 of the Agrobacterium tumifaciens strain ATCC 15955.

Figure 8:
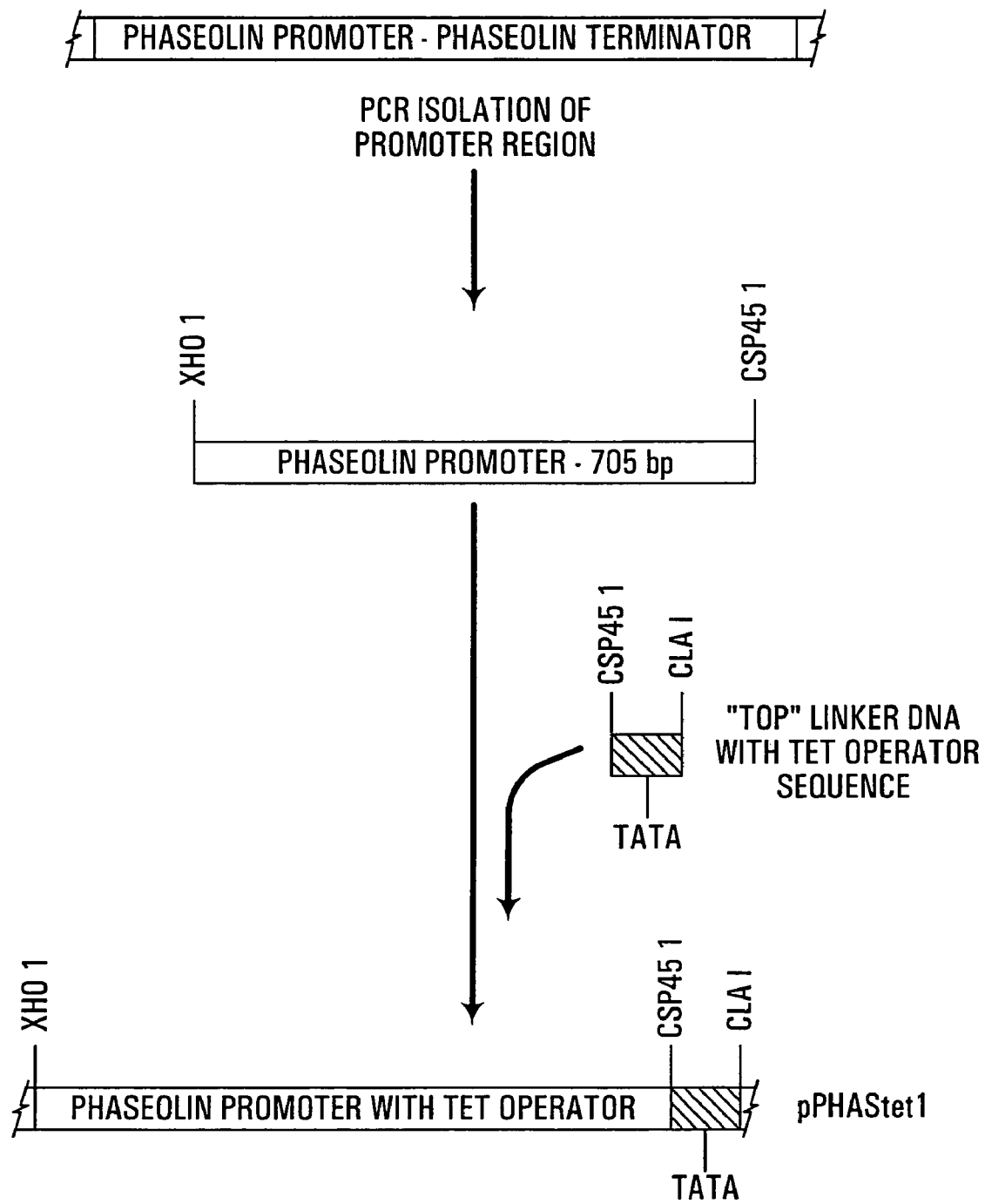

FIG. 8 illustrates the construction of the seed specific promoter, the phaseolin promoter, modified to contain a bacterial repressor binding site. The vector containing this modified promoter is pPHAStet1.

Figure 9A:
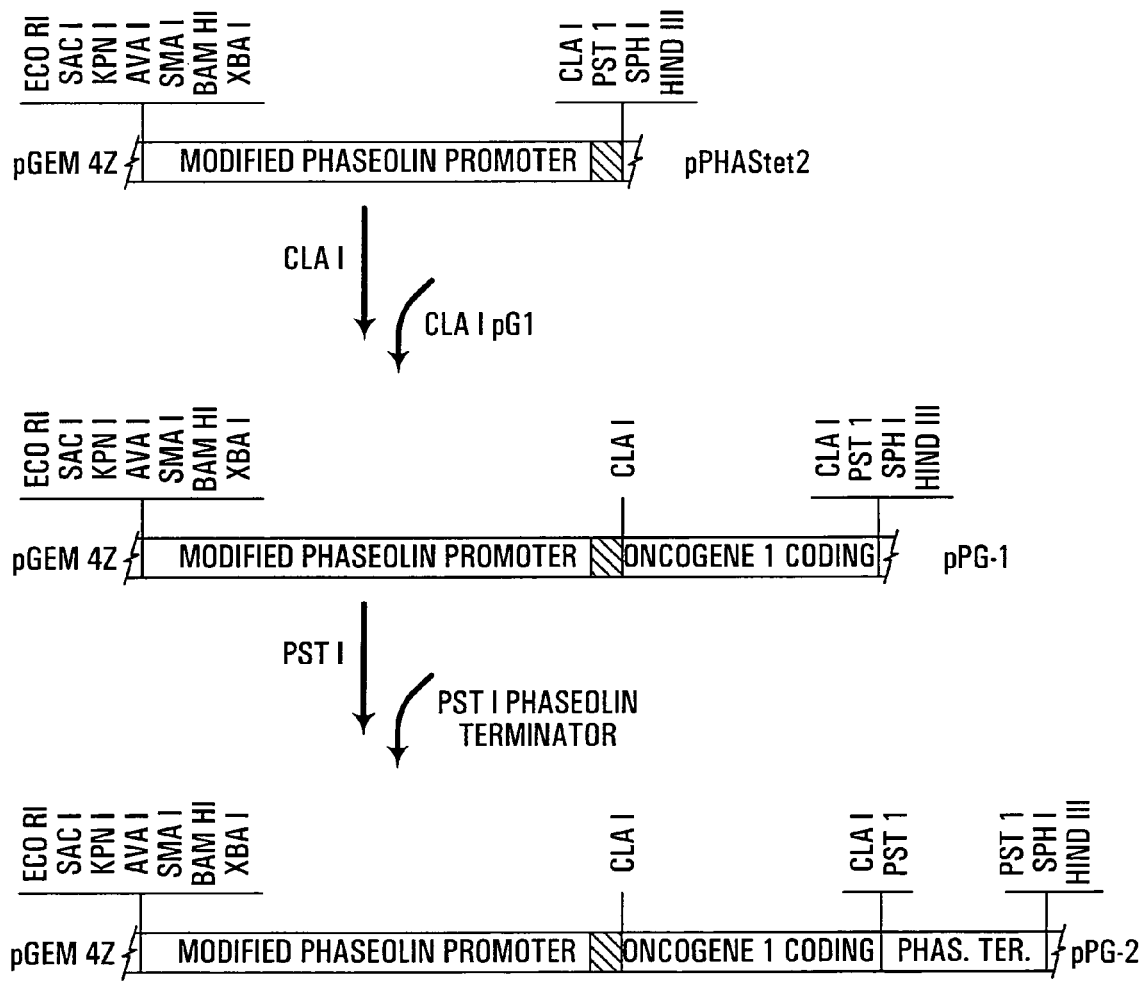
Figure 9B:
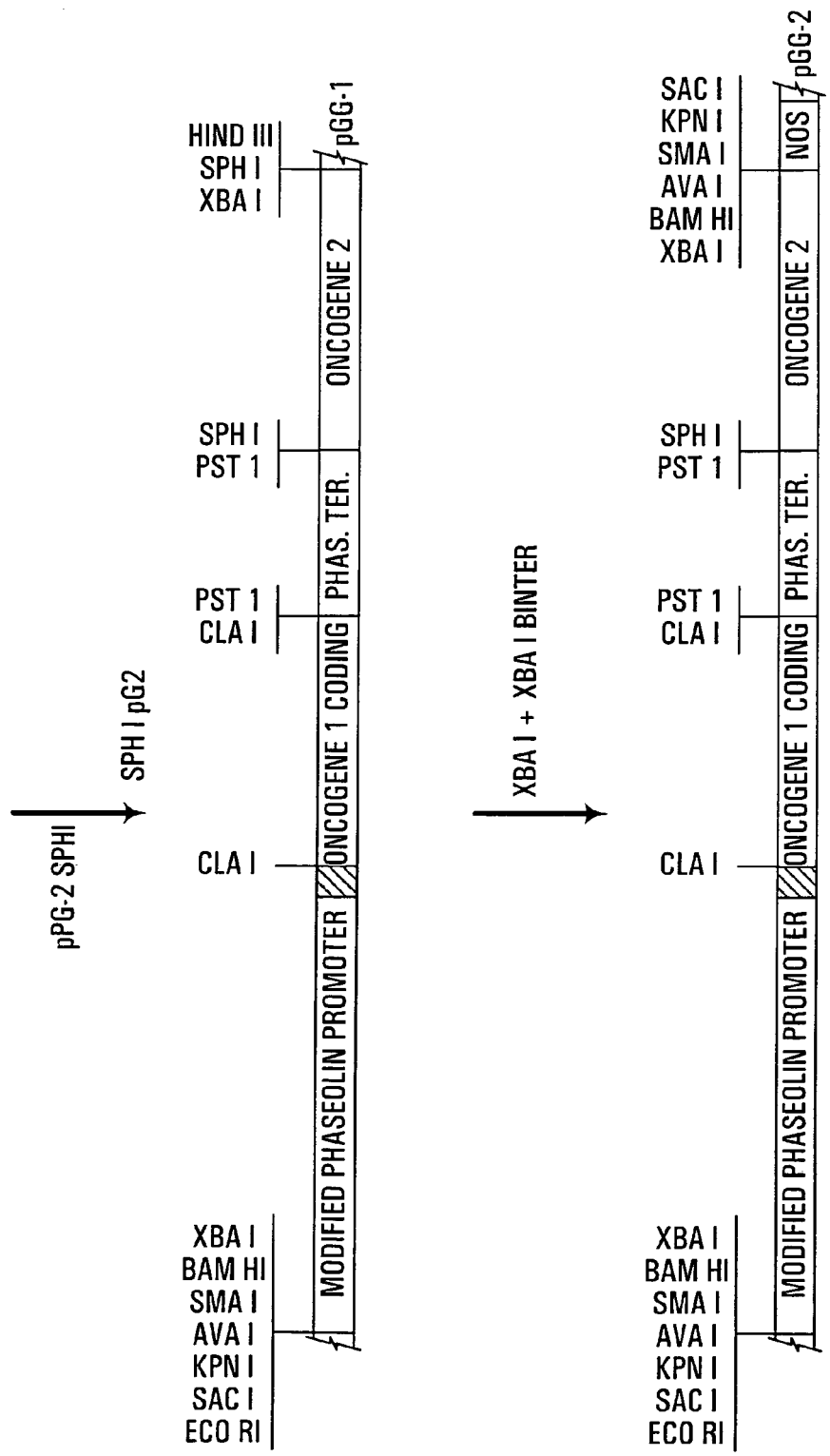

FIGS. 9A and 9B illustrate the construction of a plant transformation vector comprising: 1) the oncogene 1 of Agrobacterium lumifaciens Ti plasmid pTi15955 under the control of the phaseolin promoter modified to contain a bacterial repressor binding site (FIG. 9a) and, (2) the conditionally lethal gene, oncogene 2, under the control of its native promoter (FIG. 9b).

Figure 10:
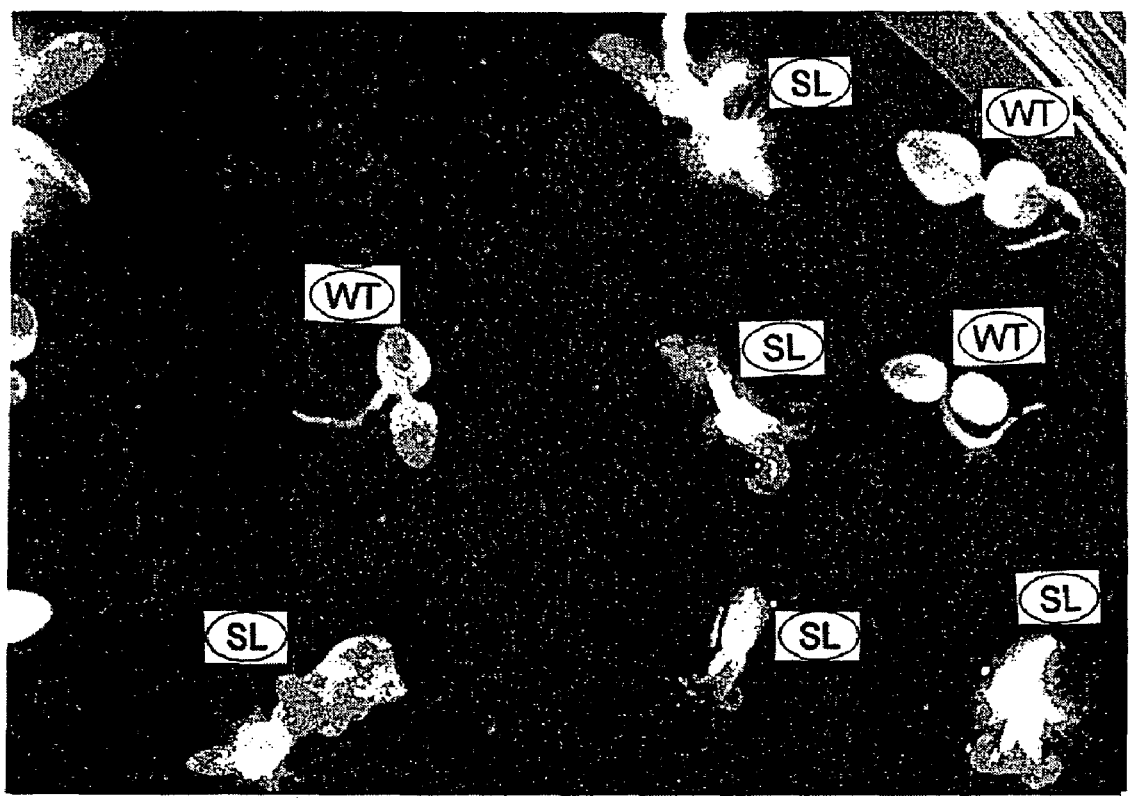

FIG. 10 shows the germination of wild-type (WT) seeds compared to seeds containing a repressible seed lethal gene without a repressor gene (the seed lethal or SL phenotype).

Figure 11:
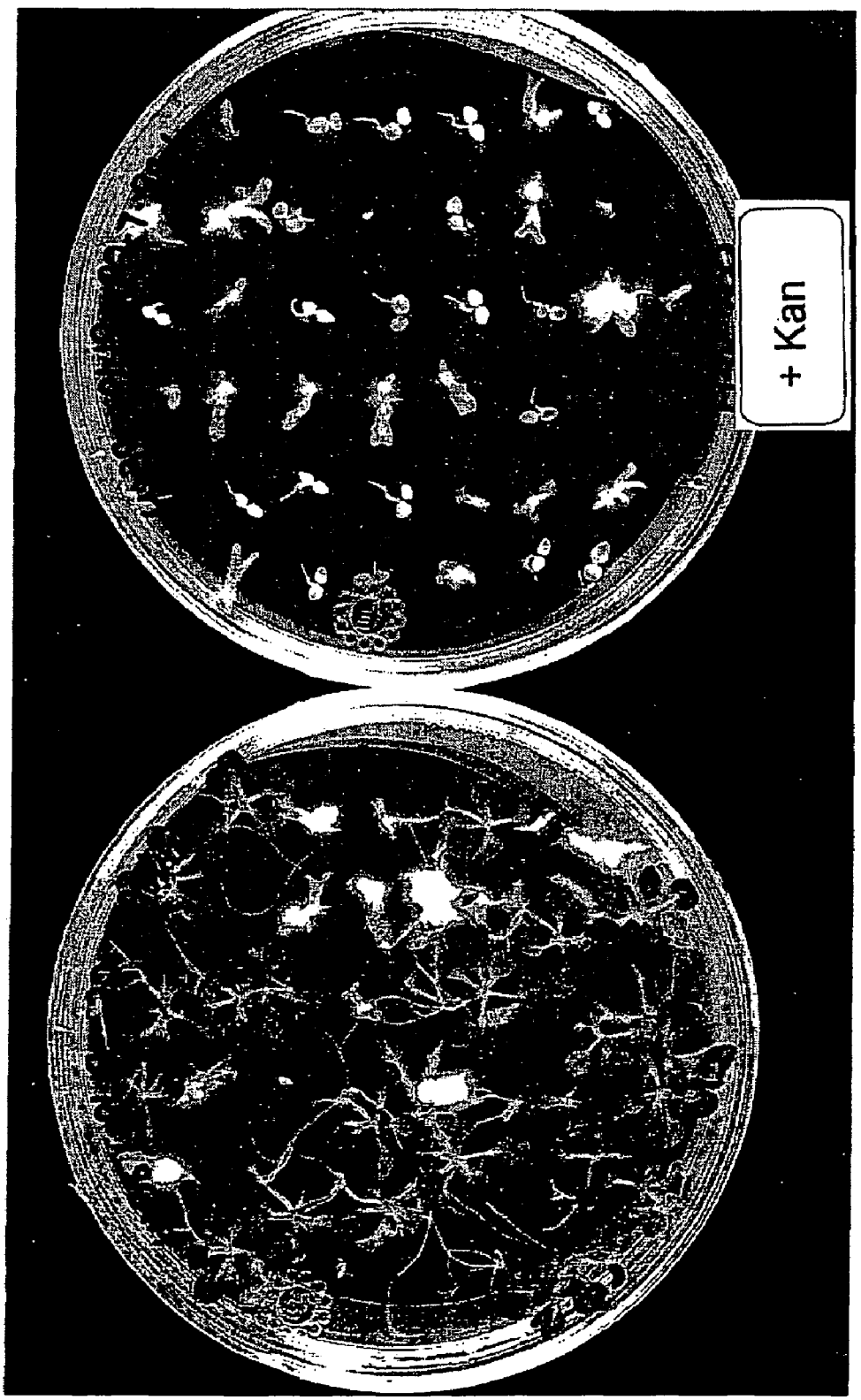

FIG. 11 shows wild-type plantlets, as well as plantlets of a segregating population of plants containing a repressible seed lethal gene germinated under selective and non-selective conditions.

Figure 12:

FIG. 12 provides a comparison of plants containing a repressible seed lethal gene (A); plants containing a repressor gene (B); plants containing a repressible seed lethal gene and a repressor gene (C); and wild-type plants (D).

DESCRIPTION OF THE SPECIFIC EMBODIMENTS

In accordance with the subject invention, methods and compositions are provided for a novel means of producing transgenic plants wherein the transfer and persistence of recombinant genes via pollen from said plants to other cultivars or related species is substantially reduced. Additionally, the methods permit the production of self pollinating plant lines which carry DNA constructs that restrict outcrossing of the germplasm and, furthermore, restrict the introgression of alien germplasm even in sexually compatible plant species.

Accordingly, the method provides genetic isolation and identity preservation of the germplasm which contains recombinant molecules comprising repressible lethal genes and repressor genes. The method further allows a means to remove recombinant plants from any growing location by application of a chemical agent or exposure of the plants to a physiological stress.

In a first embodiment, the invention provides a method comprising:

I.) Preparing a first DNA expression cassette that comprises, in addition to the DNA sequences required for transformation and selection in plant cells, a DNA sequence that encodes a product that is harmful or disruptive to cells such that death of cells and ultimately death of the entire plant occurs (a lethal gene). Expression of the lethal gene is regulated by an appropriate promoter, preferably a seed specific promoter. Said lethal gene construct additionally comprises DNA elements responsive to a repressor wherein expression of the lethal gene activity is blocked in the presence of said repressor molecule. A gene encoding a trait of interest (novel trait) can be linked to the lethal gene;

II.) Preparing a second DNA expression cassette that comprises, in addition to the DNA sequences required for transformation and selection in plant cells, a repressor gene that encodes a repressor molecule capable of blocking the expression of the lethal gene activity contained in the first DNA expression cassette. Expression of the repressor gene is regulated by a promoter active in plant cells, preferably a promoter that is expressed in all plant cells, more preferably a promoter that is expressed at a level and time sufficient to inhibit the expression of the lethal gene, and, III.) Inserting the recombinant DNA described in (I) and (II) into a plant cell capable of being transformed, regenerating the cell into a whole plant, and recovering a plant which contains the DNA of (I) and (II) at positions in the plant genome wherein the DNA of (I) and (II) assorts independently during meiosis.

The gene encoding a "novel trait" can be any recombinant protein or peptide of interest. Typically this "novel trait" is a heterologous protein of commercial interest or a protein that confers an agronomically useful trait such as herbicide tolerance. Transfer of the novel trait through crossing with native or cultivated sexually compatible plants which lack the repressor is limited because the lethal phenotype appears in the seed, leading to abortion of seeds which have received the novel trait gene. It is further contemplated that the lethal gene activity can comprise a single encoded product or two or more independent gene products that act cooperatively to express the lethal phenotype.

To maximize independent assortment, commonly referred to as "segregation", of the repressible lethal DNA and repressor constructs during meiosis, the recombinant DNA molecules are located on different chromosomes. Standard methods of transformation are known to result in random insertion of recombinant DNA within the plant genome; thus it is expected that in the majority of plants the recombinant DNAs will be located on different chromosomes. Independent assortment of genes and the location of inserted DNA are determined by simple well known methods.

Seed increases of plants with the repressible lethal and repressor constructs located on different chromosomes can be made by simple selfing in isolation, provided that the plants are homozygous for the two recombinant DNA constructs. Such homozygous plants can be obtained by selfing primary transformants, or by anther or microspore culture if the transformation procedure is carried out with diploid tissues. Alternatively, such plants can be obtained directly via transformation of microspores or other haploid cells followed by chromosome doubling. It is apparent to those skilled in the art that plant lines homozygous for both the repressible lethal gene and the repressor can be obtained by crossing isogenic transformed plant lines comprising either the repressible lethal gene or the repressor. Alternatively a combination of simple tissue culture techniques such as anther culture and sexual crossing can be employed to recover plants homozygous for both inserted DNAs.

Said homozygous plants described above may be grown on a commercial scale as an open-pollinated crop. The out-crossing of such plants to non-recombinant sexually compatible plants produces a first generation of plants heterozygous for the recombinant traits. In subsequent generations of out-crossed plants the independent segregation of genes during meiosis will result in a rapid decline in the incidence of plants expressing the novel trait. Additionally a variation of the method is contemplated such that the repressible lethal-novel trait construct further comprises a conditionally lethal gene. Plants comprising such a gene construct may be removed if required by activating the lethal phenotype, e.g. by chemical spray.

The homozygous plants described above may be grown on a commercial scale as a hybrid crop if such plants also comprise a pollination control system that allows hybrid seed formation. Such a pollination control system could be any of the known types of male sterility systems such as cytoplasmic male sterility, self-incompatibility or genic male sterility. Additionally male sterility may in some species be achieved by mechanical means or may result from the application of chemicals that specifically kill pollen (gametocides). The choice of the appropriate system will vary with the individual crop species. Such methods are well known to those skilled in plant breeding. The use of plants homozygous for the repressible-lethal and repressor recombinant gene constructs as either a male or female parent in a hybrid cross will result in hybrid seed heterozygous for the recombinant DNA constructs. Segregation of these constructs in the F2 and subsequent generations will result in the rapid loss of plants comprising the introduced novel recombinant trait.

Random insertion of recombinant DNA will on some occasions result in the incorporation of said recombinant DNAs on opposite chromosomes of a homologous chromosome pair. The frequency of occurrence of such events is dependent on the number of chromosome pairs comprising the genetic constitution of a given plant and will occur with greatest frequency in plants with small numbers of chromosome pairs. The introduction of the recombinant DNA constructs to different members of a homologous chromosome pair has the advantage that during meiosis, segregation of the repressible lethal-novel and repressor constructs occurs immediately and completely such that, provided that recombination due to crossing over has not occurred, no plants containing both constructs are formed as a result of out-crossing. This particular variation of the invention is particularly suited to development of recombinant crops wherein the trait of interest, (e.g. production of hormones or other pharmaceutically active molecules) needs to be very tightly controlled.

Seed increases of plants wherein the recombinant DNA constructs have inserted into different members of a homologous chromosome pair require that the plant cells are essentially heterozygous with respect to the repressible lethal gene and the repressor, to ensure repression of the lethal phenotype. This can easily be achieved by linking the repressible lethal gene to a selectable marker gene that confers resistance to a specific chemical. The use of herbicide resistance genes for the maintenance and selection of plants carrying specific recombinant traits is well documented in the literature and can be employed in the present invention. Any gene that confers field level resistance can be used. It is also possible for a chosen gene, such as the phosphothricin acetyl transferase (pat) gene conferring tolerance to phosphinothricin, to be used for selection during transformation. Plants comprising said genetic constructs are selfed and seed grown out under field conditions and sprayed with herbicide. Plants homozygous for the repressible-lethal novel trait (25%) will be killed by the action of the lethal gene in the absence of the repressor. Plants homozygous for the repressor gene (25%) will be killed by the action of the herbicide. In contrast, plants containing both the repressible lethal-novel gent and the repressor gene (50%) will be unaffected. Linkage of a novel trait gene to the repressible lethal gene ensures that the novel trait gene can not form viable seed by inadvertent transfer of pollen to any unintended sexually compatible species. Persistence of the novel trait in unintended plant populations is therefore completely restricted.

For some applications, control of spread of the novel trait is optimal if two repressible lethal genes and repressor genetic constructs are employed.

According to this aspect of the invention, methods and compositions are provided for a novel means of producing transgenic plants that contain two recombinant repressible lethal gene constructs. All plants comprising recombinant DNA resulting from outcrossing of the transgenic plant are rapidly eliminated from the environment. The first repressible lethal gene construct comprises a lethal gene and a repressor gene that blocks the expression of a second repressible lethal gene and optionally a gene encoding a novel trait of interest. The second repressible lethal gene construct comprises a second lethal gene and a repressor gene that blocks the expression of the first repressible lethal gene. Cells containing both genetic constructs produce two types of repressor molecules; hence both lethal genes remain in a repressed state. Segregation of the genetic constructs during meiosis results in separation of repressor and lethal genes resulting in ultimate death of all plants containing any recombinant DNA from the plant which originally contained the two repressed lethal genes.

Thus, in accordance with another aspect of the invention, methods are provided for a novel means of producing transgenic plants, comprising:

I.) Preparing a first DNA expression cassette that comprises, in addition to the DNA sequences required for transformation and selection in plant cells, a first lethal gene. Expression of the first lethal gene is regulated by an appropriate promoter, preferably a seed specific promoter. This first lethal gene expression cassette contains a first repressor responsive site, allowing expression of the lethal gene to be inhibited by a first repressor molecule. Optionally, linked to the first DNA expression cassette is a third DNA expression cassette comprising a dominant conditionally lethal gene and a fourth DNA expression cassette comprising a second repressor gene encoding a second repressor that is functionally distinct from the first repressor molecule and is capable of inhibiting expression of a second lethal gene. A gene encoding a novel trait may also be included;

II.) Preparing a second DNA expression cassette that comprises, in addition to the DNA sequences required for transformation and selection in plant cells, a first repressor gene that encodes a first repressor molecule capable of inhibiting the expression of the lethal gene contained in the first DNA expression cassette. Linked to the second DNA expression cassette is a fifth DNA expression cassette comprising a second repressible lethal gene, the expression of which is repressed by the second repressor molecule contained in fourth DNA cassette; and III.) Inserting the recombinant DNA described in (I) and (II) into a plant cell capable of being transformed, regenerating the cell into a whole plant, and recovering a plant which contains the DNA of (I) and (II) at positions in the plant genome wherein the DNA of (I) and (II) segregates during meiosis and outcrossing.

The first, third or fourth DNA cassette can be linked to a gene encoding a novel trait such as but not limited to, a recombinant protein or peptide of commercial or agronomic interest. The resultant transgenic plants would carry a trait whose capacity to persist in native or cultivated sexually compatible plants is substantially diminished. This is because the latter plants lack the repressor. Any seed resulting from the union would therefore express the lethal gene and be aborted. Accordingly, persistence of either recombinant DNA of (I) or (II) in an unintended genotype (i.e. not comprising the complete recombinant DNA complement) is inhibited. Plants which contain the first (I) recombinant DNA may also be discriminated by the use of the conditionally lethal marker gene.

It is further contemplated that the lethal gene activity can comprise a single encoded product or two independent gene products that act cooperatively to express the lethal phenotype. It is further noted that the conditionally lethal gene may comprise a product that can act in both in cooperation with said repressed lethal gene to express the lethal phenotype or in response to exogenously applied substances that can be acted upon directly to cause the expression of the lethal phenotype.

The foregoing embodiments rely on the random insertion of DNA during the transformation process to achieve the placement of the two recombinant DNAs at loci which segregate during meiosis. This is achieved as a result of simple crossing and progeny analysis, or by mapping of the inserted DNA using any techniques widely practiced by plant breeders. Accordingly a desired genetic combination is obtained.

However, it is within the scope of the present invention to introduce simultaneously all the required DNA expression cassettes within a single molecule, and then use a transposase to transpose the desired cassette(s) Specific transposition can occur by providing the appropriate combinations and orientations of DNA sequences recognized by a recombination-enzyme such as a transposase.

Known transposons and associated transposase activities include Ac/Ds and En/Spm elements from maize (e.g. see Federoff, N. Maize Transposable Elements. In Berg, D. E. and Howe, M. M. (eds) Mobile DNA, pp. 375-411, American Society for Microbiology, Washington, D.C., 1989), Tam-1 and Tam-3 from snapdragon (e.g. see Sommer et al, Transposable Elements of *Antirrhinum majus*. In Plant Transposable Elements, O. Nelson, ed, Plenum Press, New York, pp. 227-235, 1988), Tnt-1 from tobacco (Pouteau, S. et al, Mol Gen Genet. 228:233-239, 1991), Tph-1 from petunia (Gerats A. G. M. et al, The Plant Cell. 2:1121-1128, 1991) and the Tst-1 element from potato (Koster-Topfer, et al, Plant Mol. Biol. 14:239-247,1990).

Some transposons may have transposition characteristics that are of particular use in the present invention. For example, Ds elements have a tendency to transpose over relatively short distances on the same chromosome (Dooner and Belachew, Genetics 122:447-457, 1989, Dooner et al, The Plant Cell 3:473-482, 1991, Jones et al, The Plant Cell 2:701-707, 1990, Osborne et al, Genetics 129:833-844, 1991, Rommens et al, Plant Molecular Biology, 20: 61-70, 1992). Such a transposition pattern would facilitate recovery of a genetic combination where a transposed repressor is transposed to a site on the opposite chromosome of a chromosome pair that carries the repressible lethal gene.

Accordingly, use of a specific transposase enzyme to move a repressor gene to a genetic locus that segregates independently from the repressible lethal gene is provided as follows:

A DNA construct is modified to contain, in addition to a first repressible lethal gene, a repressor gene linked to the first repressible lethal gene. The repressor gene is further modified by having at its 3' and 5' ends specific DNA sequences recognizable by a transposase enzyme. The recognition sequences are oriented in such a fashion as to permit the excision of the repressor gene by a transposase. The transposase further catalyzes the reinsertion of the excised repressor gene to a random location in the genome such that the repressor gene segregates independently from the first repressible lethal gene.

The transposase enzyme can be transiently introduced into the plant cell, or be placed under the control of an inducible promoter such that induction of transposition can occur. Alternatively, the transposase may be introduced by simple sexual crossing with an isogenic or near isogenic plant line which has been modified to express active transposase.

Alternatively, for those embodiments which employ the use of two repressed lethal genes and two independent repressors, the following method is provided as follows:

A DNA construct is modified to contain, in addition to a first repressible lethal gene linked to a second repressor, a second repressible lethal gene linked to a first repressor. The second repressible lethal gene and first repressor are linked together and bounded at the 3' and 5' end by specific DNA sequences recognizable by a transposase enzyme. The recognition sequences are oriented in such a fashion as to permit the excision of the linked second repressible lethal gene-first repressor gene sequence by a transposase enzyme. The transposase further catalyzes the reinsertion of the excised gene sequence to a random location in the genome such that the linked second repressible lethal gene—first repressor gene sequence segregates independently from the linked first repressible lethal gene—second repressor gene sequence.

The transposase activity can be provided by any means including transient expression of introduced DNA, direct injection of the transposase enzyme, or more preferably, by simple sexual crossing with an isogenic or near isogenic plant line which has been modified to express active transposase.

Simple crossing and selection allow the selection of plant lines that contain both repressed lethal genes but do not contain the transposase enzyme. Linkage of the transposase enzyme to an easily identifiable marker gene can facilitate selection of the desired genetic combinations. A desired combination comprises the repressed lethal gene and the repressor gene on opposite sister chromosomes of a chromosome pair.

It is within the scope of the invention to use site specific recombination sequences to obtain site-specific insertion of repressor and repressed lethal genes. Many site specific recombinases have been described in the literature (Kilby et al., Trends in Genetics, 9(12): 413-418, 1993). Three recombinase systems that have been extensively employed: an activity identified as R encoded by the pSR1 plasmid of *Zygosaccharomyes rouxii*, FLP recombinase encoded by the 2 μm circular plasmid from *Saccharomyces cerevisiae* and Cre-lox from the phage P1. All of these recombinase systems have been shown to function in heterologous hosts. For example R has been demonstrated to work in tobacco cells (Onouchi et al., Nucl. Acids. Res. 19(23):6373-6378, 1991). FLP has been shown to be functional in tobacco and *Arabidopsis* (Kilby et al., The Plant Jour. 8(5):637-652, 1995), and Cre-lox has been shown to be functional in tobacco (Russell et al., Mol. Gen. Genet. 234:49-59, 1992, Odell et al., Mol. Gen. Genet. 223:369-378, 1990, Dale and Ow, Gene 91:79-85, 1990, Dale and Ow, Proc. Natl. Acad. Sci. USA 88:10558-10562, 1991, Haaren and Ow, Plant Molecular Biology 23:525-533, 1993). It is within the scope of the present invention to target introduced DNA to a specifically defined locus using the integration function of site-specific recombinases.

The use of site specific recombinases for directing homologous recombination in higher cells is well documented. For example, Fukushige and Sauer (Proc. Natl. Acad. Sci. USA, 89:7905-7909, 1992) demonstrated that the Cre-lox homologous recombination system could be successfully employed to introduce DNA into a predefined locus in mammalian cells. In this demonstration a promoter-less antibiotic resistance gene modified to include a lox sequence at the 5' end of the coding region was introduced into Chinese hamster ovary cells. Cells were re-transformed by electroporation with a plasmid that contained a promoter with a lox sequence and a transiently expressed Cre recombinase gene. Under the conditions employed, the expression of the Cre enzyme catalyzed the homologous recombination between the lox site in the chromosomally located promoter-less antibiotic resistance gene and the lox site in the introduced promoter sequence leading to the formation of a functional antibiotic resistance gene. The authors demonstrated efficient and correct targeting of the introduced sequence; 54 of 56 lines analyzed corresponded to the predicted single copy insertion of the DNA due to Cre catalyzed site specific homologous recombination between the lox sequences.

Use of the Cre-lox system to specifically excise, delete or insert DNA has been demonstrated in plants (Dale and Ow, Gene 91:79-85, 1995). The precise event is controlled by the orientation of lox DNA sequences. In cis, the lox sequences direct the Cre recombinase to either delete (lox sequences in direct orientation) or invert (lox sequences in inverted orientation) DNA flanked by said sequences, while in trans the lox sequences can direct a homologous recombination event resulting in the insertion of a recombinant DNA. Accordingly, within the present invention a lox sequence may be first introduced into the genome of a plant cell and regenerated to a whole plant. The lox sequence serves as an "anchor" or a recombinase target DNA sequence to permit the subsequent introduction of a recombinant DNA construct comprising a repressed lethal gene or a repressor gene or a combination thereof. Said lox sequence may be optimally modified to further comprise a selectable marker which is inactive but which can be activated by insertion of a sequence into the lox site. It is within the scope of the present invention to insert into a plant cell a promoterless marker gene linked to the lox sequence. The DNA which is to be subsequently inserted into the target lox site is modified to contain a promoter containing a lox site such that insertion of the DNA results in the joining of the promoter to the promoterless marker gene, thereby activating the marker gene. The Cre recombinase gene can be introduced simultaneously with the DNA insert into the plant such that insertion of the recombinant DNA into the target lox site by homologous recombination abolishes expression of the Cre gene.

According to the present invention, site-specific insertion of recombinant DNA into plant comprises:

Inserting into the genome of a transformable plant a DNA construct comprising a DNA sequence recognized by a site specific recombinase (i.e. a recombinase target DNA sequence), and recovering a plant containing said sequence. The transformed plant is then made homozygous for the recombinase target DNA sequence by selfing and selection or by anther or microspore culture as described above.

Subsequently the homozygous plants are transformed independently with:

I.) A first DNA expression cassette that comprises, in addition to the DNA sequences required for transformation and selection in plant cells, (1) a sequence that can be recognized and used by a site specific recombinase to insert said DNA at a specific DNA sequence, and (2) a repressible lethal gene. The expression of the repressible lethal gene is regulated by an appropriate promoter, preferably a seed specific promoter. A gene encoding a novel protein or trait may be included as part of said first expression cassette;. and, II.) A second DNA expression cassette that comprises, in addition to the DNA sequences required for transformation and selection in plant cells, (1) a sequence that can be recognized and used by a site specific recombinase to insert said DNA at a specific DNA sequence, and (2) a repressor gene that encodes a repressor molecule capable of blocking the expression of the lethal gene activity contained in the first DNA expression cassette. Expression of the repressor gene is regulated by a promoter functional in plant cells, preferably a promoter that functions in all plant cells, and more preferably a promoter that functions at a level and time sufficient to inhibit expression of the lethal gene.

After transformation, plants are recovered which have integrated the sequences defined in (I) or (II) above into their genome. A recombinase function is introduced into the plants either in trans or by activation of a pre-existing recombinase gene to excise the DNAs described in I and II above and re-insert them at the recombinase target DNA sequence. Plants containing re-inserted recombinant DNA are recovered. These plants now contain either the repressible lethal gene or the repressor gene at the same locus.

Sexual crosses are carried out between the plants containing either the repressible lethal gene or the repressor gene. From those sexual crosses, plants are selected that contain both the repressible lethal gene and the repressor gene located at the same locus on opposite chromosomes of a homologous chromosome pair.

For some embodiments of the invention, it maybe preferable to first transform a plant cell with the DNA encoding a recombinase enzyme which further comprises the recombinase target DNA sequence. The recombinase gene may be under the control of a constitutive or tissue specific promoter or a promoter whose expression can be conveniently regulated such that the expression of the gene and subsequent site specific integration of the repressed lethal and repressor genes can be induced at a specific time.

In accordance with another aspect of the subject invention, methods and compositions are provided for a novel means of producing recombinant plants that contain in addition to the fore-mentioned first and second DNA expression cassettes, a third DNA expression cassette that comprises a dominant conditionally lethal gene to allow plants containing the conditionally lethal gene to be killed by exposure to a chemical agent. Preferably the conditionally lethal gene is linked to the first DNA expression cassette.

The DNA construct comprising said linked first and third DNA cassettes may further comprise a target gene encoding a novel protein or trait. Such a novel trait cannot be transferred outside of the genotype into which it was introduced by crossing with native or cultivated sexually compatible plants. As these plants lack the repressor, any seed resulting from the union would be inviable. Plants containing the novel trait can also be discriminated by the use of the conditionally lethal marker gene. Accordingly, even in plant populations which may have inadvertently received the repressor gene, the conditionally lethal gene may be used to eliminate plants which may comprise both repressor and repressed lethal gene.

It is further noted that the conditionally lethal gene may comprise a product which can act both in cooperation with said repressed lethal gene to express the lethal phenotype or in response to exogenously applied substances that can be acted upon to cause the expression of the lethal phenotype.

In the foregoing embodiments, segregation is used to limit the persistence or spread of a novel trait or germplasm to unintended populations.

In the most elemental form of the present invention, segregation of the repressible lethal gene, linked to a trait of interest, from the repressor gene blocks the formation of viable seed comprising the trait of interest in unintended populations through cross pollination. Under typical agricultural conditions, if the trait of interest is linked to a repressible lethal gene, under the control of a seed-specific promoter, then persistence of the trait in an unintended plant or plant population, is rapidly diluted by 75% per generation in plants capable of selfing. In this predictive model, by the F5 generation of unintended plant population that has been cross pollinated by a plant comprising a repressible lethal gene and a repressor, the persistence of the trait of interest linked to the repressible lethal gene in an unintended population approaches zero. Two simple genetic models are presented, one for plants that are primarily self pollinating, e.g., *Brassica napus*, and plants that are primarily self-incompatable, e.g. *Brassica rapa*.

Simple Genetic Model for the System in a Selfing Plant

| | |
|---|---|
| SL = Repressible Lethal Gene under the control of a seed-specific promoter linked to a gene of interest. | |
| R = Repressor | |
| Homozygous Repressible Seed Lethal, Repressor Plant genotype: | SL/SL, R/R |
| Crossed with an untransformed wild plant: | –/–, –/– |
| Results in a hemizygous wild plant population comprising hemizygous lines. | SL/–, R/– |

If this wild plant population is a selfing plant population the following progeny result:

| Theoretical progeny analysis off a selfing hemizygous plant | | | | |
|---|---|---|---|---|
| Haploid gametes | SL, R | SL, – | –, – | –, R |
| SL, R | SL/SL, R/R[1] | SL/SL, –/R[2] | SL/–, R/–[3] | SL/–, R/R[4] |
| SL, – | SL/SL, R/–[5] | SL/SL, –/–[6] | SL/–, –/–[7] | SL/–, –/R[8] |
| –, – | SL/–, R/–[9] | SL/–, –/–[10] | –/–, –/–[11] | –/–, –/[12] |
| –, R | SL/–, R/R[13] | SL/–, R/–[14] | –/–, R/–[15] | –/–, R/R[16] |

| Persistence of the gene linked to the SL trait in the population | | |
|---|---|---|
| | Plants: | |
| | With | Without |
| [1]1/16 are SL/SL, R/R homozygous. | .0625 | .0000 |
| [6, 7, 10]3/16 carry only the seed lethal trait, they are reproductive dead ends | .0000 | .1875 |
| [4, 13]2/16 carry a homozygous repressor, heterozygous SL, only half of the seed carries the SL gene | .0625 | .0625 |
| [2, 5]2/16 carry a homozygous SL, hemizygous R, only half of the seed survives | .0625 | .0625 |
| [11, 12, 15, 16]4/16 have no SL gene | .0000 | .2500 |
| 2/16 are hemizygous for SL, homozygous for R, this represents a one half loss of the SL gene | .0625 | .0625 |
| Totals | .2500 | .7500 |

Therefore the loss of the trait linked to the SL gene is 75% per generation in a selfing population. This is based on the loss of the trait with the expression of the SL in seed.

However, if the hemizygous plant is a predominantly outcrossing (or self-incompatible) plant, the persistence of a gene linked to the SL trait is considerably lower. This is shown below.

Simple Genetic Model for the System in an Outcrossing Plant

Homozygous Repressible Seed lethal,

| | |
|---|---|
| Homozygous Repressible Seed lethal, Repressor Plant: | SL/SL, R/R |
| Crossed with an untransformed wild plant: | –/–, –/– |
| Results in a hemizygous wild plant population comprising hemizygous lines. | SL/–, R/– |

| Theoretical progeny analysis of a selfing hemizygous plant | | | | |
|---|---|---|---|---|
| Haploid gametes | SL, R | SL, − | −, − | −, R |
| −, − | SL/−, R/−[1] | SL/−, −/−[2] | −/−, −/−[3] | −/−, −/R[4] |
| −, − | SL/−, R/−[5] | SL/−, −/−[6] | −/−, −/−[7] | −/−, −/R[8] |
| −, − | SL/−, R/−[9] | SL/−, −/−[10] | −/−, −/−[11] | −/−, −/R[12] |
| −, − | SL/−, R/−[13] | SL/−, −/−[14] | −/−, /−[15] | −/−, −/R[16] |

| Persistence of the gene linked to the SL trait in the population | | |
|---|---|---|
| | Plants: | |
| | With | Without |
| [1, 5, 9, 13]4/16 are SL/−, R/− hemizygous, only 75% of the population can be expected to carry a SL and R combination (4/16 × .75) | .0625 | .1875 |
| [2, 6, 10, 14]4/16 carry only the seed lethal trait, they are reproductive dead ends | .0000 | .2500 |
| [3, 7, 11, 15]4/16 have no SL gene | .0000 | .2500 |
| 4/16 are hemizygous for R, no SL gene | .0000 | .2500 |
| Totals | .0625 | .9375 |

Therefore a plant population that is predominant outcrossing will rapidly lose a gene linked to the SL trait at a rate of 93.73% per generation.

It is clear from these models that the SL trait confers a selective disadvantage for maintenance of a gene encoding a trait of interest linked to the repressible lethal gene in an unmanaged population (i.e. populations where the combination of repressible lethal gene and repressor are not maintained). It should be noted that unmanaged populations can include sexually compatible wild species as well as sexually compatible cultivated species.

In one embodiment, the repressible lethal gene is expressed by a seed specific promoter. This allows for sexual crossing of independently transformed repressible lethal and repressor lines. By using the repressible lethal line as a female parent, only seed derived from introduction of the repressor gene will be formed, confirming the complete repression of the seed lethal trait. In those seeds where repression is incomplete and hence commercially of limited value seed abortion will occur. Accordingly, this embodiment of the method provides a convenient means to select via conventional crossing the most useful genetic compositions.

A seed specific promoter also confers certain advantages over a constitutive promoter for the regulation of the lethal trait. First, plants that contain the seed lethal trait can be easily converted to homozygous lines after the introduction of the repressor gene, as follows. A plant grown from a seed formed by the sexual introduction (or simultaneous introduction) of the repressor and repressible seed lethal gene can be subjected to anther or isolated microspore culture to directly recover a homozygous plant line. Alternatively, conventional methods such as crossing and selection of homozygous lines may be used to recover the appropriate plant lines.

In some instances the final product or plant line for commercial purposes may be the hemizygous combination of the repressible lethal gene and the repressor gene. According to one aspect of the invention, a method is provided for improving hybrid seed production in self-incompatible crops using self-incompatibility. Current methods of hybrid seed production often employ two self-incompatible lines, one of which acts as a "female" parent while the other functions as a "male" parent. Under ideal conditions seed formed on the female parent represents hybrid seed formed as a result of pollination by the male parent which is also self-incompatible but compatible with the female parent. However, such a system is prone to contamination due to the inadvertent breakdown of self-incompatibility resulting in self-pollination on the female parent. Accordingly, use of a repressible lethal gene under the control of a seed specific promoter in the female parent blocks the formation of selfed seed since the seed lethal trait is expressed in selfed seed. Providing the repressor gene via the pollen of the male parent line allows formation of viable hybrid seed that carries a repressible lethal gene and a repressor gene.

The female parent can be increased by clonal propagation. Alternatively, since certain physical or chemical treatments can overcome self-incompatibility, use of an inducible repressor gene repronsive to these conditions would be advantageous. Although some of these conditions may occur naturally in the field and would be of limited value for practicing the invention, some conditions such as salt stress or high levels of carbon dioxide which are known to overcome self-incompatibility in Brassica species, could be employed. Alternatively, a repressor active only under certain conditions (e.g. a repressor that binds to a DNA sequence in the presence of a particular substance) could be utilized in increasing the seed of the female parent. Many such repressors may be found in the art. As described, a variety of means may be employed to increase the female parent when desired it is noted that final product of a hybrid cross is seed that carries a repressible lethal gene from the female parent and a repressor gene from the male parent. Said seed can further comprise a novel trait linked to said repressible lethal gene.

In the context of the present invention any mechanism that effectively blocks accumulation of the product of the lethal gene in a cell comprises repression. Such a mechanism may include the binding of a specific "repressor protein or factor" to a DNA region or "operator" within the promoter of said lethal gene. Examples in the art include but are not limited to bacterial repressors and associated DNA binding regions (operator DNA) such as the Lac Z repressor, the tet repressor, the class of repressor proteins that regulate sugar catabolism in bacterial systems (van Rooijen, R. J. and de Vos, W. M., J. Biol. Chem. 265:18499-18503, 1990), including LacR, GutR, DeoR, FucR and GlpR, or the Agrobacterium repressor known as accR that regulates the biosynthesis of agrocinopines and conjugal transfer (Bodman et al., Proc. Natl. Acad Sci USA 89:643-647, 1992). Other sources of repressors can be employed including those found in fungi such as yeast or any other organism. According to the present invention, the repressor is capable of binding a specific DNA sequence present in a region of a plant promoter, said binding capable of substantially inhibiting expression of a DNA sequence under the control of said modified promoter.

It is understood that optimal expression of heterologous genes' in plant cells may require certain modifications. Typically these include: alteration of the coding sequence to reflect the usual plant codon preferences; elimination of sequences that may be poorly recognized by plant-transcriptional or translational machinery; addition of translational enhancers or stabilizing sequences; and addition of DNA sequences encoding localization signals such that the protein encoded by said gene is correctly compartmentalized. Accordingly, for some repressors of bacterial origin, these modifications may be required in order to achieve sufficient expression levels of the repressor to allow for complete repression of the repressible gene.

Other DNA binding proteins that have been modified to bind strongly to specific DNA sequences, the so-called "transdominators", may also be employed as repressors. Other repressors may include antisense RNA directed to the lethal gene, or specific inhibitors of the product of the lethal gene. An example is "Barstar", a specific inhibitor of the ribonuclease Barnase which is toxic when expressed in plant cells.

It is contemplated that down-regulation of the lethal gene can be accomplished in some instances by the use of co-suppression, as long as segregation of the transgene responsible for co-suppression of the lethal phenotype restores the lethal phenotype. Accordingly repression in the context of this invention comprises any mechanism which reversibly inhibits the expression of the lethal phenotype.

The DNA encoding said repressible lethal gene additionally comprises a promoter region regulating the expression of said lethal gene. Although the preferred embodiment comprises a seed specific promoter, other promoters are contemplated. Said promoter may be a constitutive promoter, an inducible promoter, or a tissue specific promoter and may comprise a operator sequence (repressor binding sequence) for binding a specific repressor protein such that in the presence of said repressor proteins transcription of said lethal gene is blocked. The choice of promoter will be apparent to those skilled in the art and will be a promoter that in particular is known to be expressed in the plant species in which the invention is to be employed.

In accordance with still another aspect of the subject invention, methods and compositions are provided for a novel means of producing recombinant plants that contain a conditionally lethal gene such that plants containing said gene and recombinant DNA molecules can be killed by exposure to a chemical agent. The chemical agent has no effect on other plants. This mechanism completely eliminates spread of the recombinant DNA to other cultivars of the same species and related species via pollen mediated out-crossing. Conditionally lethal genes have been described in the art and those that act directly upon a non-toxic substance to convert said substance into a toxic substance are contemplated within the scope of the present invention.

It is further understood that a conditionally lethal gene may also simply comprise a repressible lethal gene capable of de-repression by a exogenously applied substance or a artificial or naturally induced physiological stress. Accordingly, in one specific embodiment, a conditionally lethal gene comprises a lethal gene activity which is repressed by the binding of a DNA binding protein. Repression can be lifted by a specific substance that abolishes the binding. An example includes the bacterial tet repressor, whose binding to the operator sequence is blocked by tetracycline. In this case, segregation de-represses the lethal gene activity during out-crossing or introgression, while the gene can be further utilized as a conditional lethal gene to eliminate plants containing the recombinant DNA constructs by exposure of the plants to tetracycline.

It is further understood that de-repression of the lethal gene activity can also be carried out by inhibition of the expression of the repressor gene. For example, antisense RNA or ribozymes capable of inhibiting the expression of the repressor gene can be employed. It is preferable to have such an "anti-repressor" gene under the control of an inducible promoter. Examples of inducible promoters that may be employed within the scope of the present invention include those inducible by a simple chemical such as the promoter of the 27 kD subunit of the maize glutathione-S-transferase (GST II) gene (PCT/GB90/00110) or PR promoters such as PR-1a, PR-1b, PR-1c, PR-1, PR-Q, PR-S or the cucumber chitinase gene promoter, or the acidic and basic tobacco β-1,3 glucanase promoters. Numerous chemicals capable of inducing these and related promoters are described in EP89/103888.7.

Limiting the pollen-mediated movement of a target gene encoding a novel trait involves linkage of the target gene to a repressible lethal gene that is segregated away from the repressor gene in pollen after meiosis. Activation of the repressible lethal phenotype occurs after segregation of the lethal gene from the recombinant DNA encoding the controlling or repressing element. Accordingly, elimination of the transfer of the target gene to unintended sexually compatible plants is achieved. The use of a seed specific promoter to control the expression of the repressed lethal gene leads to non-viable seeds which results from cross-pollination with pollen that carries the trait gene and lethal gene that expresses in the seed in the absence of the repressor. Use of a seed specific promoter to limit the expression of the repressible lethal gene also permits the production of pollen which ensures seed set on the recombinant plant.

Limiting the pollen-mediated movement of all recombinant DNA molecules including both the trait gene linked to the repressible lethal gene and the independently segregating repressor gene involves inclusion of a second repressible lethal gene as a component of the first repressor gene. In this scheme, both recombinant DNAs that segregate independently during meiosis carry a lethal gene; however, each lethal gene is repressed by a distinct repressor. Accordingly, the seed-specific lethal phenotype linked to the target gene is repressed by the independently segregating corresponding repressor gene while expression of the second repressible lethal gene linked to said independently segregating repressor gene is repressed by a second repressor gene now linked to the trait gene. The plant therefore carries two repressible lethal genes, each under the control of a functionally different repressor. Accordingly, one or the other or both lethal genes are derepressed following meiosis and outcrossing. As a result, seed cells formed by outcrossing or introgression of alien germplasm are inviable.

Expression of the trait of commercial interest introduced by transformation may be regulated by a constitutive, inducible or developmentally regulated promoter that may be the same or different from the promoter regulating the lethal or conditionally lethal phenotype. The choice of promoter will vary in relation to the given commercial application.

For specific aspects of the present invention where the trait of commercial interest is the production of heterologous proteins that are to be isolated from plant tissues, a developmentally regulated promoter functional in developing seeds is a logical choice. Many different types of cell, tissue and developmentally regulated promoters are described in the literature from which those appropriate to the trait of commercial interest may be selected. Additionally, methods to discover and characterize new promoters that may be used in specific embodiments of the present invention are well known.

DNA encoding the novel trait can be a gene which gives rise to a detectable phenotype such as modified oil, meal, starch or other seed component. Alternatively, it may be a gene which confers a particular agronomic trait such as herbicide tolerance or insect or pest resistance. The gene may also encode a protein that imparts no detectable phenotype or a protein with pharmaceutical or industrially useful activity. The DNA encoding the novel trait can be expressed under the control of a number of different promoters, depending on the trait. It is obvious to the skilled artisan that a number of strategies can be employed for the expression of a novel trait.

For preferred embodiments of the present invention wherein the recombinant target protein of commercial interest is to be produced in and recovered from plant seeds, the first expression cassettes includes a recombinant DNA sequence comprising a transcriptional and translational regulatory region specifically capable of expression in developing plant seeds, and more specifically seed embryo or other seed tissue capable of triglyceride storage, and a second recombinant DNA sequence encoding a chimeric peptide or protein comprising a sufficient portion of an oil-body specific protein to provide targeting to an oil body, the target protein of commercial interest and a transcriptional and translational termination region functional in plants. The chimeric peptide or protein may also comprise a peptide sequence linking the oil-body specific portion and the target protein of commercial interest that can be specifically cleaved by chemical or enzymatic means.

DNA expression cassettes may be so constructed that the DNA sequences comprising the transcriptional and translational regulatory regions and the DNA encoding both the target, repressor and lethal genes be linked by multiple cloning sites to allow for the convenient substitution of alternative target, repressor and lethal DNA sequences.

As preferred embodiments of the subject invention, the repressible lethal gene activity is the oncogenes 1 and 2 from the Ti or R1 plasmid of *Agrobacterium*. The activity of these two genes combined leads to the production of IAA and plant cell death.

Oncogene 1 encodes the enzyme Indole Acetamide Synthase (IAMS) that converts tryptophan, an amino acid normally found in plant cells to indole acetamide. The function of oncogene 1, that is the conversion of tryptophan (a endogenous amino acid contained within all plant cells) to indole acetamide is described by VanOnckelen et al., FEBS lett. 198, 357-360, 1986.

Oncogene 2 encodes the enzyme Indole Acetamide Hydrolase (IAMH) which converts indole acetamide to indole acetic acid. The function of gene 2, that is the ability to convert indole acetamide to indole acetic acid, was demonstrated by Tomashow et al., Proc. Natl. Acad. Sci. USA 81, 5071-5075, 1984 and Schroder et al., Eur. J. Biochem. 138, 387-391, 1984. Specifically oncogene 2 in concert with oncogene 1 provide for the synthesis of the plant growth regulator indole acetic acid from tryptophan via a pathway found in bacterial cells but not in plant cells. Related oncogene activities are found in *A. rhizogenes, A. vitis* (Canaday, J. et al., Mol. Gen. Genet. 235:292-303, 1992) and *Pseudomonas savastanoi* (Yamada et al., Proc. Natl. Acad. Sci. USA, 82:6522-6526, 1985).

The preferred use of oncogenes is based on the known fact that they are naturally occurring activities that overproduce a substance normally found in plant cells and, that unlike lethal activities associated with toxins such as diptheria toxin A chain, ribonucleases such as Barnase and ribosome inhibiting proteins such as ricin and related toxins, the repression of the genetic activity need not be absolute. It has been suggested that exceeding low levels of expression, even one molecule per cell of powerful cytotoxic agents such as ricin can lead to cell death. It is noted that in order to use such powerful toxins within the scope of this invention, repression of the repressed lethal phenotype needs to be complete and methods are employed to achieve that level of repression by functional assay.

Although complete repression can be easily achieved within the scope of this invention, such as the use of DNA binding proteins or repressors, or specific inhibitors of toxin activity (Barnase and Barstar for example) the use of a lethal gene activity that over-expresses a growth regulator offers the opportunity to utilize a number of different repression schemes within the scope of the invention. Included are antisense RNA or ribozyme inhibition of the expression of the lethal genes, preferably targeted to gene 1 or gene 1 and gene 2; co-suppression, preferably using a gene encoding a homologous sequence to gene 1; or expression of an enzyme capable of metabolizing or conjugating excess IAA. Such enzymatic activities are known in the art.

The substrate for gene 2, indole acetamide, is not normally produced by plant cells. In addition to the conversion of indole acetamide, gene 2 is capable of the metabolism of other indole amides including the synthetic chemical naphthalene acetamide resulting in the formation of the powerful auxin analog naphthalene acetic acid (NAA). Application of NAM (naphthalene acetamide) to plant cells expressing the gene 2 product IAMH produce lethal concentrations of NAA. Accordingly oncogene 2 can function as a conditionally lethal gene. However, within the scope of the present invention, oncogenes 1 and 2 preferentially comprise the lethal gene activity.

The use of both IAMS in combination with IAMH has been described as a means to selectively ablate pollen in methods of hybrid seed production (U.S. Pat. No. 5,426,041). The possibility of using recombinant non-native oncogene 2 alone as a conditionally lethal gene linked, in a random fashion, to a nuclear encoded male sterility, has been suggested as was the use of the same recombinant oncogene 2 to eliminate unwanted transgenic plants (U.S. Pat. No. 5,180,873). However, the use of the oncogene 2 alone, without the activity of oncogene 1, fails to cause a lethal gene activity. Additionally the use of the oncogene 2 as a method to remove transgenic plants requires the application of a chemical agent in order to selectively eliminate cells containing the recombinant DNA.

By contrast, the present invention provides the inherent elimination of plants which have inadvertently received foreign DNA without the need for intervention. The method further employs the overexpression of a compound naturally found in plant cells to impart the lethal phenotype which ensures environmental safety. Accordingly the invention also provides a conditionally lethal phenotype when the oncogenes 1 and 2 are used to practice the invention. In particular the unmodified, native oncogene 2 is employed.

In addition to oncogene 1 and 2, the use of oncogene 4 is contemplated. Oncogene 4 of the Ti plasmid of *Agrobacterium* sp. encodes the enzyme isopentyl transferase capable of synthesizing cytokinin, another natural plant growth regulator. Overexpression of cytokinin can lead to cell death and hence is a lethal gene activity within the scope of this invention. The growth of crown gall tumors on plants following infection by *Agrobacterium* sp. is thought to result from the overexpression of both cytokinins and auxins due to the combined activities of oncogenes 1 and 2, and oncogene 4.

It is within the scope of the present invention that the activity of both oncogenes 1 & 2 and oncogene 4 be repressed and employed. This would require repression of both lethal gene activities. De-repression would result in the overexpression of growth regulators leading to destruction of the normal activity of the plant cell and hence blocking the ability to produce seed or to reproduce. Accordingly, traits or germplasm linked to the oncogene(s) fail to persist in the de-repressed state.

It is further contemplated that repression of oncogenes 1, 2 and 4 can be accomplished without the need to modify one of all of the native genes. For those applications which do not employ the use of a seed specific repressible lethal gene, the native promoter of the oncogenes may be employed and combined with a repressor molecule such as antisense RNA or ribozymes to inhibit the expression of the oncogene.

Although oncogenes may be used methods of the present invention are not limited by them. A variety of genes which confer lethal and conditionally lethal phenotypes can be employed within the scope of the invention, and said methods are not limited to oncogenes. Accordingly any gene which is capable of inhibiting proper functioning and/or growth and development of a plant cell is considered to be a lethal gene.

A number of strategies to functionally repress the activity of a lethal gene have been described. However, as more strategies have been described in the art, the invention is not limited by the foregoing described methods of repression. It is apparent to one skilled in the art that a variety of repression strategies may be employed within the scope of the present invention.

Any method of effecting transformation of cells and recovery of transformed plants (such as *Agrobacterium* mediated DNA transfer or biolistic methods) can be used to introduce the DNA constructs within the scope of the present invention. The invention is not dependent on the method of transformation. It is further noted that the introduction of the repressible lethal gene or repressor into various plant lines may also be practiced by inserting the recombinant DNAs concomitantly or in a stepwise fashion. Alternatively one may obtain the desired combination or repressible lethal and repressor genes by simple sexual crossing. In the instance where the genetic constructs are to be transferred to sexually incompatible relatives tissue culture techniques such as wide crosses and/or embryo rescue may be employed. A variety of techniques known to those skilled in the art may be employed to derive the combination of repressible lethal and repressor genes which provides the greatest utility within the scope of the present invention.

The following examples are set forth to illustrate the method and in no way limit the scope of the invention.

EXAMPLE 1

Isolation of Oncogene 1 and 2 from *Agrobacterium* Ti-plasmid pTi15955

To isolate the oncogenes, the following steps were employed. The subclones p101 and p202, detailed in U.S. Pat. No. 5,428,147 encompassing the DNA encoding oncogene 1 (p202) and oncogene 2 (p101) are used as a source of the genes. In order to isolate the genes, a combination of PCR to introduce convenient restriction sites and subcloning of native gene fragments is employed to derive oncogenes that can be conveniently inserted into plant transformation vectors.

To isolate a native oncogene 2, the following approach is used. The 5' region, including the native promoter of oncogene 2 is isolated by PCR amplification of the plasmid p101 with the following primers:

```
G2P1                                              (SEQ ID NO:1)
5' ATAGCATGCTCTAGATGTTAGAAAAGATTCGTTTTTGTG 3'
and, G2P2                                              (SEQ ID NO:2)
5' ATACCATGGCGATCAATTTTTTTGGCGC 3'.
```

G2P1 contains a Sph 1 site (boldface) and a Xba I site (underlined) and corresponds to the complement of nucleotides 5808-5785 in the published sequence of pTi15955. G2P2 contains a Nco 1 site (boldface) and corresponds to nucleotides 5285-5309 in the published sequence of pTi15955. The use of G2P1 and G2P2 yields a fragment of 523 bp which represents the 5' region of the native oncogene 2, including the promoter modified to contain a Sph 1 and Xba I site at the 5' end of the promoter.

To isolate the 3' region of oncogene 2, including the native terminator structure, two PCR primers are used. The first primer used is:

```
G2P3                                              (SEQ ID NO:3)
5' ATAAAGCTTGAAAATTAAGCCCCCCCCCG 3'
and, G2P4                                              (SEQ ID NO:4)
5' ATAGGATCCGCATGCCCAGTCTAGGTCGAGGGAGGCC 3'.
```

G2P3 contains a Hind III site (boldface) and corresponds to the complement of nucleotides 3396-3371 of the published sequence of pTi 15955. G2P4 contains a Sph 1 site (boldface) and a Bam H1 site (underlined) and corresponds to nucleotides 3237-3264 of the published sequence of pTi 15955. The use of G2P3 and G2P4 yields a fragment of 164 bp which represents a portion of the 3' end of the native oncogene 2.

The plasmid p101 is digested with Nco I and Hind III to yield a fragment of approximately 1895 bp fragment of oncogene 2 which encompasses most of the coding region. The 523 bp fragment of the 5' end of the native oncogene 2 is digested with Nco I and ligated to the Nco I site of the 1895 bp fragment and the 164 bp 3' end of the gene is digested with Hind III and ligated to the Hind III site of the 1895 bp fragment. The reconstructed native oncogene 2 is then digested with Sph 1 and subcloned into the Sph 1 site of the common cloning vector pGEM-4Z (Promega, La Jolla, Calif.). This vector is called pG2. DNA sequencing was used to verify the composition of this reconstructed DNA corresponding to the authentic DNA sequence of the native oncogene 2.

Isolation of oncogene 1 employs a combination of PCR to introduce convenient restriction sites and subcloning of a native gene fragment. To isolate the required fragments, the following approach is used. Convenient restriction sites at the 5' end of the coding region are introduced by PCR, employing the following two primers:

```
G1P1                                              (SEQ ID NO: 5)
5' ATAATCGATATAGAAACGGTTGTTGTGGTT 3'
and, G1P2                                              (SEQ ID NO: 6)
5' ATAAGATCTCGGGGAAGCGACC 3'
```

G1P1 contains a Cla 1 site (boldface) and corresponds to nucleotides 5755-5775 of the published sequence of pTi 15955. G1P2 contains a Bgl II site (boldface) and corresponds to the complement of nucleotides 6028-6010 of the published sequence of pTi 15955. G1P1 and G1P2 are used to amplify a 273 bp fragment of oncogene 1 which is modified to contain a Cla 1 site at the 5' end of the coding region.

To isolate a 3' fragment of the coding region of oncogene 1, two primers are used to introduce convenient restrictions sites at the 3' end of the coding region.

```
G1P3                                              (SEQ ID NO: 7)
5' AATGATATCTGAACTTTATGATAAGG 3'
and, G1P4                                              (SEQ ID NO: 8)
5' ATAGAGCTCATCGATACTAATTTCTAGTGCGGTAGTT 3'.
```

G1P3 contains a Eco RV site (boldface) and corresponds to nucleotides 7350-7372 of the published sequence of pTi 15955. G1P4 contains a Cla 1 site (boldface) and a Sac 1 site (underlined) and corresponds to nucleotides 8076-8056 of the published sequence of pTi 15955. The use of G1P3 and G1P4 results in a 732 bp fragment representing the 3' end of the coding region of oncogene 1.

In order to reconstruct a complete coding region of the oncogene 1, the plasmid p202 is digested with Bgl II and the 1697 bp fragment encompassing the partial coding region of the oncogene 1 is isolated. To the 5' end of this fragment is added the 273 bp PCR fragment, digested with Bgl II, resulting in a partial oncogene 1 modified to contain a Cla 1 site at the 5' end of the coding region. To reconstruct the entire oncogene 1, the 726 bp PCR fragment representing the 3' sequences is digested with Bam HI and Sac 1 and the resultant fragment is ligated to the Ban HI site at the 3' end of the 1697 bp fragment, resulting in a reconstructed oncogene 1 with Cla 1 sites at the 5' and 3' ends of the coding region and a Sac 1 site at the 3' end of the coding region. These fragments are contained within the vector pBluescript (Promega, La Jolla, Calif.). The resulting plasmid is called pG1. DNA sequencing was used to verify the composition of this reconstructed DNA corresponding to the authentic DNA sequence of the native oncogene 1.

A diagrammatic representation of the steps employed in the construction of pG1 and pG2 is shown in FIGS. 7a and 7b.

EXAMPLE 2

Construction of a Phaseolin Promoter with a Bacterial Repressor Binding Site In this example, the tetracycline (tet) operator DNA is introduced into the phaseolin promoter. In order to insert the tet operator sequence into the phaseolin promoter sequence, PCR is used to isolate the region of the promoter that corresponds the DNA sequence 5' to the native TATA box and a synthetic DNA sequence containing three copies of the tet operator sequence. The TATA box is ligated to the PCR fragment of the promoter resulting in the formation of a reconstructed phaseolin promoter containing three copies of the tet operator sequence. The means by which this is accomplished is as follows and is shown in FIG. 8.

The promoter region of the phaseolin gene (described in: Slightom, J. L., Sun, S. M. and Hall, T. C., Proc. Natl. Acad. Sci. USA 80:1897-1901, 1983) is isolated by PCR using the vector pAGM 219, kindly supplied by Dr. G. Cardineau of Mycogen Plant Sciences, San Diego, Calif. The plasmid pAGM 219 contains approximately 1600 base pairs of the promoter region of the phaseolin gene and the native termination region of the phaseolin gene. The region of the promoter 5' to the TATA box was isolated by PCR in preparation for the addition of a synthetic DNA sequence comprising the tet operator DNA and a TATA box.

The first PCR primer used was engineered to introduce a Csp45 1 site by a minor alteration of the nucleotide sequence in the native promoter sequence. The sequence of this primer is shown below:

SEQ ID NO: 9
5'GGTGGTTCGAACATGCATGGAGATTTG 3'

The Csp45 1 restriction site is shown in boldface. The second primer used for PCR has the following sequence:

SEQ ID NO: 10
5'CCGTATCTCGAGACACATCTTCTAAAGTAATTT 3'

A Xho 1 site is indicated in boldface. The PCR product obtained using these primers was called pPHAS and corresponds to nucleotides 128 - 833 of the DNA sequence of the phaseolin promoter of the lambda genomic clone AG-λPVPh177.4 (λ177.4), (Slightom, J.L., Sun, S.M. and Hall, T.C., Proc. Nati. Acad. Sci. USA 80:1897-1901, 1983). A synthetic tet operator sequence was added to this fragment by joining the synthetic duplex DNA to the Csp45 1 site in the PCR product. The synthetic operator DNA sequence also comprises a Cla 1 site at the 3' end of the sequence. The top strand of the synthetic DNA has the following sequence:

SEQ ID NO: 11
5' _TTCGAA_ACTCTATCAGTGATAGAGTGTATATAAGACTCTATCAGTG

ATAGAGTGAACTCTATCAGTGATACAGTAT _ATCGAT_ 3'

Which comprises 3 copies of the operator DNA (boldface), a TATA box (underlined), a Csp45 1 site at the 5' end (italics and underlined) and a Cia 1 site at the 3' end (italics and boldface). A bottom strand fragment is used which has the following sequence:

SEQ ID NO: 12
5'CGATATACTGTATCACTGATAGAGTTCACTCTATCACTGATAGAGTC

TTATATACACTCTATCACTGATAGAGTCTTCGTT 3'.

Which comprises a complementary strand to SEQ ID NO:9 and contains a Cla 1 cohesive end, identified in boldface. The duplex DNA is referred to a "top" DNA and is ligated to the Csp45 1 and Cla 1 cut pPHAS and clones containing the inserted "top" DNA are chosen. This vector is referred to as pPHAStet1. DNA sequencing was used to verify the composition of this reconstructed DNA.

EXAMPLE 3

Construction of a Plant Transformation Vector Comprising an Oncogene 1 Under the Control of a Modified Repressible Phaseolin Promoter Linked to an Active Oncogene 2.

In this example, formation of a plant transformation vector is described which comprises a repressible lethal gene activity resulting from the combined activity of two genes, oncogene 1 (placed under the control of the modified phaseolin promoter) and native oncogene 2. When expressed, the two oncogenes in this vector lead to the formation of excess IAA, killing plant cells in which the lethal gene activity is expressed. To construct this vector, the following steps are employed.

The plasmids pPHAStet1 and pG1 are digested with Cla 1 and the coding region for oncogene 1 is inserted into the Cla 1 site of pPHAStet1 to produce the vector pPG-1. The phaseolin terminator contained in the plasmid pAGM 219, comprising the nucleotide sequences starting at 36 bp downstream of the protein termination codon TGA comprising a Sac I site extending approximately 1400 nucleotides ending at a Pst 1 site, was further modified to introduce a Pst 1 site at the position of the Sac 1 site. This modification allows the entire terminator sequence to be excised from pAGM 219 as a Pst 1 fragment of approximately 1400 bp. This 1400 bp terminator fragment is inserted into the Pst 1 site of pPG-1 to form pPG-2, which comprises the phaseolin promoter modified to contain three tet operator DNA sequences, the coding region of oncogene 1 and the phaseolin terminator sequence.

The Sph 1 fragment of pG2 containing the native oncogene 2 is inserted into the unique Sph 1 site of pPG-2 to form the vector pGG-1. The vector pGG-1 is digested with Xba I to excise the entire insert comprising the phaseolin promoter modified to contain three tet operator DNA sequences, the coding region of oncogene 1 and the phaseolin terminator sequence, and the native oncogene 2 under the control of its own promoter. This Xba I fragment is inserted into the Xba I site of the plant transformation vector Binter.

The plant transformation vector Binter comprises the widely used plant transformation vector Bin 19 (Clontech, Palo Alto, Calif.) into which has been inserted a nos terminator fragment as follows. The nos terminator contained in the vector pBI 221 (Clontech) was first isolated as a Sac 1-Eco R1 fragment and cloned into pGEM-4Z at the Sac I and Eco R1 sites. This plasmid, pGEMter, was digested with Hind III and Eco R1 to remove the nos terminator and the entire polylinker and inserted into Hind III-Eco R1 digested Bin 19. This vector is called Binter.

Binter containing the Xba I fragment comprising the phaseolin promoter modified to contain three tet operator DNA sequences, the coding region of oncogene 1 and the phaseolin terminator sequence, and the native oncogene 2 under the control of its own promoter is referred to as pGG-2. The steps employed to construct pGG-2 are illustrated in FIG. 9.

EXAMPLE 4

Transformation of Plants to Introduce a Repressible Seed Lethal Gene Under the Control of a Modified Phaseolin Promoter In this example, tobacco plants are transformed with the vector pGG-2 using standard *Agrobacterium* mediated transformation to obtain plants which comprise a repressible seed lethal gene activity. Plants obtained were grown in the greenhouse and allowed to flower. Selfed seed was collected as well as seed derived from reciprocal crossing with wild-type tobacco. Tobacco plants that carry the repressible seed lethal gene but do not carry a repressor form seeds that are not viable as judged from germination assays. This is illustrated in FIGS. 10 and 11. In FIG. 10, a photomicrograph of germinating tobacco seeds comprising the seed lethal vector and wild-type tobacco seeds are compared. Seeds were surface sterilized and plated on basic media. Seeds were allowed to germinate. Wild-type seeds are marked "WT" and seeds comprising the seed lethal gene are identified as "SL". Wild-type seeds geminated normally, had normal cotyledons and true first leaves. "SL" plantlets had thickened cotyledons, lacked true first leaves and showed typical signs of auxin overproduction, including callus and excessive rooty phenotype. In order to provide evidence that the normal plantlets or the "WT" plantlets were devoid of the seed lethal construct, seeds from the same transformant were planted on media with and without kanamycin. Following germination on kanamycin containing media, all of the normal plantlets became bleached and died, indicating that they did not contain the seed lethal construct (that is linked to the kanamycin gene in the pGG-2 transformation vector) and hence were sensitive to kanamycin. This is shown in FIG. 11. In this experiment, the plate marked "-kan" shows a mixture of seed lethal and wild-type tobacco plantlets from seed germinated on media without kanamycin. In the plate labeled "+kan", a similar sampling of seeds of seed lethal and wild-type were germinated in the presence of 300 ugs per ml of kanamycin. The seed lethal phenotype is visible in both plates, the seed lethal plantlets have excessive roots, thickened cotyledons and lack true first leaves. In the plate without kanamycin, the wild-type seeds produce normal plantlets, on plates with kanamycin the wild-type plants can not grow and the plantlets become bleached and eventually die. All of the seed lethal plantlets remained green, even though they failed to form normal plantlets. Thus the seed lethal phenotype is dependent on the presence of the seed lethal gene. It is also clear, that based on the results of the reciprocal crosses, the seed lethal phenotype can be transmitted via pollen. Thus the seed lethal phenotype is only manifested in the seed, and does not effect other tissues of the plant.

EXAMPLE 5

Introduction of a Repressible Lethal Gene and Repressor Gene into a Plant Line

In the first portion of this example, tobacco plants that carry the repressible lethal gene under the control of a modified phaseolin promoter are used as a female parent in a cross with tobacco that was previously transformed with a gene encoding the tet repressor under the control of a $^{35}S$ promoter and is homozygous for the inserted repressor gene. Plants appear phenotypically normal (FIG. 12). In FIG. 12, plant A is a plant that contains a repressible seed lethal gene, plant B is a plant that contains a repressor gene, plant C is a plant derived by crossing plants A and B, while plant D is a wild-type tobacco plants. It should be noted that the plants are not all exactly the same age; these plants were maintained by propagation. This photograph is provided to illustrate that plants with a repressible seed lethal gene are phenotypically normal. Seed from plant C is recovered and germinated in the presence of kanamycin to select seed that contains the repressible lethal gene. Viable seed (i.e. seed that germinates normally) contains both the repressible lethal gene and a copy of the repressor gene. PCR analysis for the presence of the repressible lethal gene and the repressor confirmed the genotype. Phenotype was scored by germination analysis. A significant number of independently transformed lines were obtained and analyzed as above. Most of these independent transformed plants exhibited a seed lethal phenotype that ranged from seeds completely unable to germinate to seeds that germinated but yielded abnormal plantlets with excessive roots, thickened cotyledons and lack true first leaves. Table 1 contains the summary data from a series of crosses carried out with representative samples of these various plants. The plants identified were tested for the presence of the seed lethal gene (abbreviated as "SL" in column 2), scored for seed viability in column 3, crossed with the indicated repressor line (abbreviated as "R" in column 4), seed collected from these plants were analyzed by germination assays (as indicated in column 5) and plant tissue analyzed for the presence of the repressor and seed lethal gene. This analysis proved that repression of the seed lethal gene by the repressor permitted the formation of viable seed. Viable seed germinated normally and was found to contain both the repressible seed lethal gene and the repressor.

TABLE 1

Summary Data from Crosses of Plants Containing Repressible Seed Lethal

Genes and Plants Containing Repressor Genes.

| Column 1 Plant # | Column 2 Genotype (by PCR) | Column 3 Seed Viability | Column 4 Crossed with Repressor Plant | Column 5 Genotype (by PCR) | Column 6 Seed Viability |
|---|---|---|---|---|---|
| PL2 | SL Gene | Non-viable seed | R17-X | SL gene, R gene | Viable seed |
| PL3 | SL Gene | Non-viable seed | R17-X | SL gene, R gene | Viable seed |
| PL4 | SL Gene | Non-viable seed | R17-X | SL gene, R gene | Viable seed |
| PL5 | SL Gene | Non-viable seed | R17-X | SL gene, R gene | Viable seed |
| PL6 | SL Gene | Non-viable seed | R17-X | SL gene, R gene | Viable seed |
| PL17 | SL Gene | Non-viable seed | R17-X | SL gene, R gene | Viable seed |
| PL21 | SL Gene | Non-viable seed | R17-X | SL gene, R gene | Viable seed |
| PL38 | SL Gene | Non-viable seed | R17-X | SL gene, R gene | Viable seed |
| PL48 | SL Gene | Non-viable seed | R17-X | SL gene, R gene | Viable seed |
| PL53 | SL Gene | Non-viable seed | R17-X | SL gene, R gene | Viable seed |
| Wild type | No SL gene | Viable seed | R17-X | R gene | Viable seed |

Plant lines that contained a repressible seed lethal gene were crossed with a plant line containing a repressor gene. Segregating seed populations of both the original plant lines containing the repressible seed lethal gene and plant lines from those plants crossed with a repressor line were germinated in soil. It was found that within a segregating population of seeds derived from a plant containing a seed lethal gene, only those segregants that did not have the seed lethal gene grew. No plants were recovered that carried a seed lethal gene, proving that without the presence of a repressor, no viable plants can be formed from seeds with a seed lethal genotype. However, normal plants were recovered from the seed of crosses with a repressor. These normal plants comprised both the seed lethal and the repressor genes. This indicates that repression of the seed lethal phenotype can be achieved under normal growth conditions. When the seed lethal gene and the repressor gene segregate following crosses with wild-type plants, the seed lethal phenotype re-appears, indicating the repression has been lost through segregation. Thus these series of experiments indicates the method works as predicted based on the genetic model.

It is clear from the foregoing examples, that derivation of genetic combination comprising a repressible seed lethal gene and a repressor is within the ordinary skill of those in the art. Various modifications to the method such as derivation of homozygous lines, different crossing procedures or re-transformation of plant lines to combine the repressible lethal gene and the repressor are also apparent and are fully appreciated by the skilled artisan.

EXAMPLE 6

Production of a Homozygous Plant Line

The plants obtained in example 5, above, illustrate the utility of the method and it is appreciated that a variety of similar steps may be employed with different crops. As an illustration of how a genetic combination of the invention is achieved in a crop such as oilseed Brassica napus, this example describes the use of the method in combination with anther culture to rapidly obtain homozygous plant lines. In the present example, the first step is obtaining a plant that carries a seed lethal trait by transforming a Brassica napus plant with a recombinant DNA construct comprising a repressible lethal gene preferably linked to an easily identifiable marker gene such as the GUS gene. From a population of primary transformants of plants transformed with a single copy of a repressible lethal gene one would identify those plants in which the seed lethal trait is expressed; thus plants are unable to produce any seed that carries the genetic construct as identified by GUS screening of selfed seeds. Such a plant is then subjected to anther culture to convert the plant to a double haploid plant incapable of producing selfed seed. This plant is homozygous for the repressible lethal gene.

In order to derive a repressor-containing plant capable of repressing the seed lethal phenotype, a Brassica napus plant, preferably of the same plant variety, is transformed with a recombinant DNA construct comprising the repressor DNA. A population of plants containing said repressor DNA is selected. This population of repressor-containing plants is used as male parent to cross to the plant that expresses the seed lethal trait. To simplify the recovery of the crossed seed, it is preferable to emasculate the female parent during the cross. Viable seed produced as a result of said cross must contain the repressible lethal gene and a repressor gene capable of repressing the seed lethal phenotype. Seed from each individual cross is recovered and grown out. From this population of plants, an individual plant is selected which is capable of full self seed set and carries a repressible lethal seed trait. When cross-pollinated to other varieties lacking the repressor gene, such a plant is substantially unable to produce seeds which are positive for the GUS activity linked to said repressed lethal gene.

By such method, the genetic combination can be selected that most efficiently restricts out crossing while maintaining full self-seed set ability. It is not necessary to carry out detailed mapping of the inserted DNA, since the most favorable genetic combination will be those plants which contain the inserted DNAs in the genetic loci that most effectively segregate during meiosis. The seed from this plant line represents the original starting variety modified only to contain a repressible lethal gene and repressor gene. However said plant line is unable to substantially transfer any trait or traits associated with the repressible lethal gene.

For the production of hybrid crops such as hybrid Brassica napus, which carry a repressed lethal gene and a repressor, a modification of the method is provided to allow the production of parental lines. The most obvious approach to combining the repressible lethal gene and the repressor gene is during the production of the hybrid seed. Accordingly hybrid seed thus produced will carry the genetic composition of a repressible lethal gene and a repressor gene.

In order to accomplish the production of this genetic composition, a means to increase seed of the male parent is provided. This method includes transformation of a plant with a DNA molecule comprising a repressible lethal gene and a DNA molecule comprising a repressor gene under the control of an inducible promoter. Preferably the genes are linked and may further comprise a novel trait. The induction of the promoter allows the plant to be made homozygous for the repressed lethal gene and inducible repressor gene. Plant seeds obtained can serve as a male parent in a hybrid cross. Seed is increased in the presence of the inducer.

The female parent in said hybrid cross is produced by transforming a plant with a DNA molecule comprising a repressor gene, making the plant homozygous for the repressor gene; permitting self pollination and self-seed formation; and using this plant line as a female parent in a hybrid cross.

---

SEQUENCE LISTING

<160> NUMBER OF SEQ ID NOS: 12

<210> SEQ ID NO 1
<211> LENGTH: 39
<212> TYPE: DNA
<213> ORGANISM: Artificial Sequence
<220> FEATURE:
<223> OTHER INFORMATION: primer

<400> SEQUENCE: 1
atagcatgct ctagatgtta gaaaagattc gttttgtg                          39

<210> SEQ ID NO 2
<211> LENGTH: 28
<212> TYPE: DNA
<213> ORGANISM: Artificial Sequence
<220> FEATURE:
<223> OTHER INFORMATION: primer

<400> SEQUENCE: 2
ataccatggc gatcaatttt tttggcgc                                     28

<210> SEQ ID NO 3
<211> LENGTH: 29
<212> TYPE: DNA
<213> ORGANISM: Artificial Sequence
<220> FEATURE:
<223> OTHER INFORMATION: primer

<400> SEQUENCE: 3
ataaagcttg aaaattaagc ccccccccg                                    29

<210> SEQ ID NO 4
<211> LENGTH: 37
<212> TYPE: DNA
<213> ORGANISM: Artificial Sequence
<220> FEATURE:
<223> OTHER INFORMATION: primer

<400> SEQUENCE: 4
ataggatccg catgcccagt ctaggtcgag ggaggcc                           37

<210> SEQ ID NO 5
<211> LENGTH: 30
<212> TYPE: DNA
<213> ORGANISM: Artificial Sequence
<220> FEATURE:
<223> OTHER INFORMATION: primer

<400> SEQUENCE: 5
ataatcgata tagaaacggt tgttgtggtt                                   30

<210> SEQ ID NO 6
<211> LENGTH: 22
<212> TYPE: DNA
<213> ORGANISM: Artificial Sequence
<220> FEATURE:
<223> OTHER INFORMATION: primer

<400> SEQUENCE: 6
ataagatctc ggggaagcga cc                                           22

```
<210> SEQ ID NO 7
<211> LENGTH: 26
<212> TYPE: DNA
<213> ORGANISM: Artificial Sequence
<220> FEATURE:
<223> OTHER INFORMATION: primer

<400> SEQUENCE: 7
aatgatatct gaactttatg ataagg                                          26

<210> SEQ ID NO 8
<211> LENGTH: 37
<212> TYPE: DNA
<213> ORGANISM: Artificial Sequence
<220> FEATURE:
<223> OTHER INFORMATION: primer

<400> SEQUENCE: 8
atagagctca tcgatactaa tttctagtgc ggtagtt                              37

<210> SEQ ID NO 9
<211> LENGTH: 27
<212> TYPE: DNA
<213> ORGANISM: Artificial Sequence
<220> FEATURE:
<223> OTHER INFORMATION: primer

<400> SEQUENCE: 9
ggtggttcga acatgcatgg agatttg                                         27

<210> SEQ ID NO 10
<211> LENGTH: 33
<212> TYPE: DNA
<213> ORGANISM: Artificial Sequence
<220> FEATURE:
<223> OTHER INFORMATION: primer

<400> SEQUENCE: 10
ccgtatctcg agacacatct tctaaagtaa ttt                                  33

<210> SEQ ID NO 11
<211> LENGTH: 83
<212> TYPE: DNA
<213> ORGANISM: Artificial Sequence
<220> FEATURE:
<223> OTHER INFORMATION: primer

<400> SEQUENCE: 11
ttcgaagact ctatcagtga tagagtgtat ataagactct atcagtgata gagtgaactc     60
tatcagtgat acagtatatc gat                                             83

<210> SEQ ID NO 12
<211> LENGTH: 81
<212> TYPE: DNA
<213> ORGANISM: Artificial Sequence
<220> FEATURE:
<223> OTHER INFORMATION: primer
<220> FEATURE:
<223> OTHER INFORMATION: primer

<400> SEQUENCE: 12
cgatatactg tatcactgat agagttcact ctatcactga tagagtctta tatacactct     60
atcactgata gagtcttcgt t                                               81
```

The invention claimed is:

1. A method of producing a genetically modified plant, comprising:
   (a) providing at least one plant cell capable of being transformed and being generated into a whole plant;
   (b) introducing into the at least one plant cell:
      (I) a repressible lethal gene encoding a gene product having an activity lethal to plant cells, wherein said repressible lethal gene is selected from the group consisting of: a gene encoding the protein encoded by oncogene 1 of *Agrobacterium*; a gene encoding the protein encoded by oncogene 2 of *Agrobacterium*; and a gene encoding the protein encoded by oncogene 4 of *Agrobacterium*; and
      (ii) a sense repressor gene encoding a protein capable of repressing the activity of the gene product of the repressible lethal gene; wherein a DNA operator sequence is in operable association with the repressible lethal gene, the DNA operator sequence adapted for binding the gene product of the repressor gene to repress transcription of the gene product of the repressible lethal gene;
   (c) generating a plurality of whole plants from the at least one plant cell; and
   (d) selecting for a genetically modified plant descended from or derived from at least one of the plurality of whole plants by determining incorporation and mutually independent segregation of the repressor gene and the repressible lethal gene within the genetically modified plant.

2. The method of claim 1, wherein said introducing further comprises providing the repressible lethal gene in a first vector construct and providing the repressor gene in a second vector construct, and further comprising crossing at least two plants of the plurality of whole plants prior to said selecting.

3. The method of claim 1, wherein said determining mutually independent segregation of the repressor gene and the repressible lethal gene comprises determining that the repressible lethal gene and the repressor gene are located on respective opposite sister chromosomes of a chromosome pair of a plant cell of the genetically modified plant.

4. The method of claim 1, further comprising providing a tissue-specific promoter in transcriptional control of at least one of the repressible lethal gene or the repressor gene.

5. The method of claim 4, wherein said providing the tissue-specific promoter comprises providing a seed-specific promoter.

6. The method of claim 5, wherein the seed-specific promoter is a phaseolin promoter.

7. The method of claim 1, further comprising providing an inducible promoter in transcriptional control of the repressor gene.

8. The method of claim 1, wherein the activity of the gene product of the repressible lethal gene comprises over-expression or under-expression of a naturally occurring plant growth regulating substance in a plant cell of the genetically modified plant.

9. The method of claim 1, further comprising linking a gene conferring a trait of interest with the repressible lethal gene in a first vector construct, and wherein said introducing comprises introducing the first vector construct to the at least one plant cell.

10. The method of claim 1, wherein said generating the plurality of whole plants comprises generating at least one plant which is homozygous for the repressible lethal gene and the repressor gene.

11. The method of claim 10, further comprising crossing the at least one plant which is homozygous for the repressible lethal gene and the repressor gene with a second plant to produce the genetically modified plant.

12. A method of producing a genetically modified plant having at least one repressible lethal gene expressed during outcrossing or introgression of alien germplasm, comprising:
   (a) providing a plant cell capable of being transformed and being regenerated to a whole plant;
   (b) introducing into the plant cell:
      (I) a first repressible lethal gene under transcriptional control of a seed-specific promoter, the first repressible lethal gene encoding a gene product having a first gene product activity lethal to plant cells, wherein said first repressible lethal gene is selected from the group consisting of: a gene encoding the protein encoded by oncogene 1 of *Agrobacterium*; a gene encoding the protein encoded by oncogene 2 of *Agrobacterium*; and a gene encoding the protein encoded by oncogene 4 of *Agrobacterium*;
      (ii) a first operator sequence in operable association with the first repressible lethal gene;
      (iii) a first bacterial repressor gene, the first bacterial repressor gene encoding a protein capable of repressing the first gene product activity by binding to the first operator sequence;
      (iv) a second repressible lethal gene under transcriptional control of a seed-specific promoter, the second repressible lethal gene encoding a gene product having a second gene product activity lethal to said plant cells, wherein said second repressible lethal gene is selected from the group consisting of: a gene encoding the protein encoded by oncogene 1 of *Agrobacterium*; a gene encoding the protein encoded by oncogene 2 of *Agrobacterium*; and a gene encoding the protein encoded by oncogene 4 of *Agrobacterium*;
      (v) a second operator sequence in operable association with the second repressible lethal gene;
      (vi) a second repressor gene, the second repressor gene encoding a protein capable of repressing the second gene product activity by binding to the second operator sequence;
      (vii) at least one gene conferring a trait of interest linked to at least one of the first and second repressible lethal genes;
   (c) regenerating a whole plant from the plant cell; and
   (d) selecting for a genetically modified plant descended from or derived from the whole plant by determining incorporation and mutually independent segregation of the first repressor gene from the first repressible lethal gene, and by determining incorporation and mutually independent segregation of the second repressor gene from the second repressible lethal gene within the genetically modified plant.

13. The method of claim 12, wherein said introducing further comprises providing the first repressible lethal gene, the at least one gene conferring the trait of interest, the first operator sequence and the second repressor gene in a first genetic construct, and providing the second repressible lethal gene, the second operator sequence and the first repressor gene in a second genetic construct.

14. The method of clam 12, wherein said introducing comprises introducing the first repressible lethal gene, the first operator sequence, the at least one gene conferring the trait of interest, the second repressor gene, the second repressible lethal gene, the second operator sequence and the first repressor gene to the plant cell in a single transformation vector.

15. A method of producing a genetically modified plant having at least one repressible lethal gene expressed during outcrossing or introgression of alien germplasm, comprising:
 (a) providing a plant cell capable of being transformed and being regenerated to a whole plant;
 (b) introducing into the plant cell:
  (I) a repressible lethal gene under transcriptional control of a seed-specific promoter, the repressible lethal gene encoding a gene product having a gene product activity lethal to plant cells, wherein said repressible lethal gene is selected from the group consisting of: a gene encoding the protein encoded by oncogene 1 of *Agrobacterium*; a gene encoding the protein encoded by oncogene 2 of *Agrobacterium*; and a gene encoding the protein encoded by oncogene 4 of *Agrobacterium*;
  (ii) an operator sequence in operable association with the first repressible lethal gene;
  (iii) a bacterial repressor gene, the bacterial repressor gene encoding a protein capable of repressing the lethal gene product activity by binding to the operator sequence;
  (iv) at least one gene conferring a trait of interest linked to the repressible lethal gene;
 (c) regenerating a whole plant from the plant cell; and
 (d) selecting for a genetically modified plant descended from or derived from the whole plant by determining incorporation and mutually independent segregation of the repressor gene from the repressible lethal gene.

16. A plant, or a descendant, cell, tissue, or part thereof, comprising:
 (I) a repressible lethal gene encoding a gene product having an activity lethal to plant cells, wherein said repressible lethal gene is selected from the group consisting of: a gene encoding the protein encoded by oncogene 1 of *Agrobacterium*; a gene encoding the protein encoded by oncogene 2 of *Agrobacterium*; and a gene encoding the protein encoded by oncogene 4 of *Agrobacterium*; and
 (ii) a sense repressor gene encoding a protein capable of repressing the activity of the gene product of the repressible lethal gene;
said repressible lethal gene and said repressor gene being stably integrated into the genome of said plant such that said repressible lethal gene segregates independently from said repressor gene.

17. A plant comprising at least one plant cell derived from or descended from a genetically modified plant produced by the method of claim 12, said plant cell comprising:
 (I) a first repressible lethal gene under transcriptional control of a seed-specific promoter, the first repressible lethal gene encoding a gene product having a first gene product activity lethal to plant cells, wherein said first repressible lethal gene is selected from the group consisting of: a gene encoding the protein encoded by oncogene 1 , of *Agrobacterium*; a gene encoding the protein encoded by oncogene 2 of *Agrobacterium*; and a gene encoding the protein encoded by oncogene 4 of *Agrobacterium*;
 (ii) a first operator sequence in operable association with the first repressible lethal gene;
 (iii) a first bacterial repressor gene, the first bacterial repressor gene encoding a protein capable of repressing the first gene product activity by binding to the first operator sequence;
 (iv) a second repressible lethal gene under transcriptional control of a seed-specific promoter, the second repressible lethal gene encoding a gene product having a second gene product activity lethal to said plant cells, wherein said second repressible lethal gene is selected from the group consisting of: a gene encoding the protein encoded by oncogene 1 of *Agrobacterium*; a gene encoding the protein encoded by oncogene 2 of *Agrobacterium*; and a gene encoding the protein encoded by oncogene 4 of *Agrobacterium*;
 (v) a second operator sequence in operable association with the second repressible lethal gene;
 (vi) a second repressor gene, the second repressor gene encoding a protein capable of repressing the second gene product activity by binding to the second operator sequence; and
 (vii) at least one gene conferring a trait of interest linked to at least one of the first and second repressible lethal genes;
said first and second repressible lethal genes and said first and second repressor genes being stably integrated into the genome of said plant such that said first repressible lethal gene segregates independently from said first repressor gene and said second repressible lethal gene segregates independently from said second repressor gene.

18. A plant comprising at least one plant cell derived from or descended from a genetically modified plant produced by the method of claim 15, said plant cell comprising:
 (I) a repressible lethal gene under transcriptional control of a seed-specific promoter, the repressible lethal gene encoding a gene product having a gene product activity lethal to plant cells, wherein said repressible lethal gene is selected from the group consisting of: a gene encoding the protein encoded by oncogene 1 of *Agrobacterium*; a gene encoding the protein encoded by oncogene 2 of *Agrobacterium*; and a gene encoding the protein encoded by oncogene 4 of *Agrobacterium*;
 (ii) an operator sequence in operable association with the repressible lethal gene;
 (iii) a bacterial repressor gene, the bacterial repressor gene encoding a protein capable of repressing the lethal gene product activity by binding to the operator sequence; and
 (iv) at least one gene conferring a trait of interest linked to the repressible lethal gene;
said repressible lethal gene and said repressor gene being stably integrated into the genome of said plant such that said repressible lethal gene segregates independently from said repressor gene.

19. A plant, or a descendant, cell, tissue, or part thereof, comprising:
 (a) a repressible lethal gene encoding a gene product having an activity lethal to plant cells, wherein said repressible lethal gene is selected from the group consisting of: a gene encoding the protein encoded by oncogene 1 of *Agrobacterium*; a gene encoding the protein encoded by oncogene 2 of *Agrobacterium*; and a gene encoding the protein encoded by oncogene 4 of *Agrobacterium*;
 (b) an operator sequence in operable association with said repressible lethal gene; and
 (c) a bacterial repressor gene encoding a protein capable of repressing said repressible lethal gene by binding to said operator sequence;
said repressible lethal gene and said repressor gene being stably integrated into the genome of said plant such that said repressible lethal gene segregates independently from said repressor gene.

20. The plant or descendant, cell, tissue, or part thereof according to claim 19, wherein said repressible lethal gene and said repressor gene are located on respective opposite sister chromosomes of a chromosome pair of said plant.

21. The plant or descendant, cell, tissue, or part thereof according to claim 19, wherein said repressible lethal gene comprises a gene encoding the protein encoded by oncogene 1 of *Agrobacterium* and a gene encoding the protein encoded by oncogene 2 of *Agrobacterium*.

22. The plant or descendant, cell, tissue, or part thereof according to claim 19, wherein said operator sequence is a tetracycline (tet) operator sequence, and said bacterial repressor protein is a protein capable of binding said tet operator sequence.

23. The plant or descendant, cell, tissue, or part thereof according to claim 19, further comprising at least one gene conferring a trait of interest linked to said repressible lethal gene.

24. The plant or descendant, cell, tissue, or part thereof according to claim 19, wherein at least one of said repressible lethal gene and said repressor gene is under transcriptional control of a tissue-specific promoter.

25. The plant or descendant, cell, tissue, or part thereof according to claim 24, wherein said tissue-specific promoter is a seed-specific promoter.

26. The plant or descendant, cell, tissue, or part thereof according to claim 25, wherein said seed-specific promoter is a phaseolin promoter.

27. The plant or descendant, cell, tissue, or part thereof according to claim 19, which is a *Brassica* plant or descendant, cell, tissue, or part thereof.

28. The plant or descendant, cell, tissue, or part thereof according to claim 19, which is a *Brassica napus* plant or descendant, cell, tissue, or part thereof.

29. A *Brassica napus* plant, or a descendant, cell, tissue, or part thereof, comprising:
   (a) a repressible lethal gene encoding a gene product having an activity lethal to plant cells said repressible lethal gene comprising an oncogene; and
   (b) a repressor gene encoding a gene product capable of repressing the activity of the gene product of said repressible lethal gene;
      said repressible lethal gene and said repressor gene being stably integrated into the genome of said plant such that said repressible lethal gene segregates independently from said repressor gene;
   wherein said repressible lethal gene comprises a gene encoding the protein encoded by oncogene 1 of *Agrobacterium* and a gene encoding the protein encoded by oncogene 2 of *Agrobacterium*; and
   wherein said gene encoding the protein encoded by oncogene 1 of *Agrobacterium* is under transcriptional control of a phaseolin promoter modified to comprise a tetracycline (tet) operator sequence, and said repressor protein is a bacterial protein capable of binding said tet operator sequence.

30. The plant or descendant, cell, tissue, or part thereof according to claim 16, wherein said repressible lethal gene comprises a gene encoding the protein encoded by oncogene 1 of *Agrobacterium* and a gene encoding the protein encoded by oncogene 2 of *Agrobacterium*.

31. The plant or descendant, cell, tissue, or part thereof according to claim 16, further comprising at least one gene conferring a trait of interest linked to said repressible lethal gene.

32. The plant or descendant, cell, tissue, or part thereof according to claim 16, wherein at least one of said repressible lethal gene and said repressor gene is under transcriptional control of a tissue-specific promoter.

33. The plant or descendant, cell, tissue, or part thereof according to claim 32, wherein said tissue-specific promoter is a seed-specific promoter.

34. The plant or descendant, cell, tissue, or part thereof according to claim 33, wherein said seed-specific promoter is a phaseolin promoter.

35. The plant or descendant, cell, tissue, or part thereof according to claim 16, which is a *Brassica* plant or descendant, cell, tissue, or part thereof.

36. The plant or descendant, cell, tissue, or part thereof according to claim 16, which is a *Brassica napus* plant or descendant, cell, tissue, or part thereof.

* * * * *

UNITED STATES PATENT AND TRADEMARK OFFICE
CERTIFICATE OF CORRECTION

| | |
|---|---|
| PATENT NO. | : 7,671,253 B2 |
| APPLICATION NO. | : 10/846626 |
| DATED | : March 2, 2010 |
| INVENTOR(S) | : Fabijanski et al. |

Page 1 of 3

It is certified that error appears in the above-identified patent and that said Letters Patent is hereby corrected as shown below:

Column 12, line 11, change "lumifaciens" to -- tumifaciens --.

Column 27, lines 56-63, change

"G2P1

5' ATAGCATGCTCTAGATGTTAGAAAAGATTCGTTTTTGTG 3'"

and,

G2P2

5' ATACCATGGCGATCAATTTTTTGGCGC 3'."

to

-- G2P1 (SEQ ID NO: 1)

5' ATAGCATGCTCTAGATGTTAGAAAAGATTCGTTTTTGTG 3' and,

G2P2 (SEQ ID NO: 2)

5' ATACCATGGCGATCAATTTTTTGGCGC 3'. --.

Column 28, lines 10-15, change

"G2P3

5' ATAAAGCTTGAAAATTAAGCCCCCCCCG 3' and,

G2P4

5' ATAGGATCCGCATGCCCAGTCTAGGTCGAGGGAGGCC 3'."

to

-- G2P3 (SEQ ID NO. 3)

5' ATAAAGCTTGAAAATTAAGCCCCCCCCG 3' and,

<div style="text-align: right;">

Signed and Sealed this

Sixth Day of December, 2011

David J. Kappos
*Director of the United States Patent and Trademark Office*

</div>

G2P4 (SEQ ID NO: 4)

5' ATAGGATCCGCATGCCCAGTCTAGGTCGAGGGAGGCC 3' --.

Column 28, line 38, change "subeloning" to -- subcloning --.

Column 28, line 45, change "5' ATAATCGATATAGAAACGGTTGTTGTGGTT 3'" to

-- 5' ATAATCGATATAGAAACGGTTGTTGTGGTT 3' --.

Column 28, line 49, change "5' ATAAGATCTCGGGGAAGCGACC 3'" to

-- 5' ATAAGATCTCGGGGAAGCGACC 3' --.

Column 28, line 63, change "5' AATGATATCTGAACTTTATGATAAGG 3'" to

-- 5' AATGATATCTGAACTTTATGATAAGG 3' --.

Column 28, line 66, change "5' ATAGAGCTCATCGATACTAATTTCTAGTGCGGTAGTT 3'" to

-- 5' ATAGAGCTCATCGATACTAATTTCTAGTGCGGTAGTT 3' --.

Column 29, line 64, change "5' GGTGGTTCGAACATGCATGGAGATTTG 3'" to

-- 5' GGTGGTTCGAACATGCATGGAGATTTG 3' --.

Column 30, line 3, change "5' CCGTATCTCGAGACACATCTTCTAAAGTAATTT 3'" to

-- 5' CCGTATCTCGAGACACATCTTCTAAAGTAATTT 3' --.

Column 30, line 10, change "Nati." to -- Natl. --.

Column 30, lines 19 and 20, change

"5' TTCGAAGACTCTATCAGTGATAGAGTGTATATAAGACTCTATCAGTGATAGAGTGA ACTCTATCAGTGATACAGTAT ATCGAT 3'" to

-- TTCGAAGACTCTATCAGTGATAGAGTGTATATAAGACTCTATCAGTGAT AGAGTGAACTCTATCAGTGATACAGTATATCGAT 3' --.

Column 30, line 24, change "Cia" to -- Cla --.

Column 30, line 30, change "5' CGATATACTGTATCACTGATAGAGTTCACTCTATCACTGATAGAGTCTTATATACACTCTA TCACTGATAGAGTCTTCGTT 3'" to -- 5' CGATATACTGTATCACTGATAGAGTTCACTCTATCACTGATAGAGTCTTATATACACTCTA TCACTGATAGAGTCTTCGTT 3' --.

CERTIFICATE OF CORRECTION (continued)
U.S. Pat. No. 7,671,253 B2

Column 35, line 5, please add bibliographic information as follows

-- <110> Dow AgroSciences Canada Inc.

<120> Methods and Genetic Compositions to Limit Gene Flow and Undesired Outcrossing in Crop Plants

<130> 75151-10

<140>

<150> US 60/113545

<151> 1998-12-22

<160> 12

<170> PatentIn Ver. 2.0 --.

Column 40, line 62, change "clam" to -- claim --.